United States Patent [19]

Huse et al.

[11] Patent Number: 5,128,256

[45] Date of Patent: Jul. 7, 1992

[54] DNA CLONING VECTORS WITH IN VIVO EXCISABLE PLASMIDS

[75] Inventors: William Huse, Del Mar; Joseph A. Sorge, Rancho Sante Fe; Jay M. Short, Encinitas, all of Calif.

[73] Assignee: Stratagene, La Jolla, Calif.

[21] Appl. No.: 341,261

[22] Filed: Apr. 20, 1989

Related U.S. Application Data

[63] Continuation of Ser. No. 2,441, Jan. 12, 1987, abandoned.

[51] Int. Cl.⁵ .................. C12N 15/10; C12N 15/70
[52] U.S. Cl. .................. 435/172.3; 435/320.1
[58] Field of Search ............ 435/320.1, 172.3

[56] References Cited

PUBLICATIONS

Poustka et al., Nature, vol. 325:353-357 (1987).
Brown et al. Journal of Biol. Chem. 258:8402-8412, 1983.
J. Abraham et al.; "DNA Sequence of Regulatory Region in Integration Gene of Bacteriophage λ"; P.N.A.S., vol. 77, May 1980; pp. 2477-2481.
E. Beck and B. Zink; "Nucleotide Sequence and Genome Organosation of Filamentous Bacteriophages F1 and Fd"; Gene, vol. 16, 1981; pp. 35-58.
S. Brenner et al.; "Plasmids: Hybrids Between ColE1 Plasmids and E. Coli Bacteriophage Lambda"; Gene, vol. 17, 1982; pp. 27-44.
P. Dotto et al.; "The Functional Origin of Bacteriophage f1 DNA Replication"; 1984; J. Mol. Biol., vol. 172, pp. 507-521.
F. S. Collins et al.; "Directional Cloning of DNA Fragments at a Large Distance from an Initial Probe: A Circularization Method"; P.N.A.S. vol. 81, Nov. 1984; pp. 6812-6616.
A. A. Melnikov, et al.; "Lamba Phagemids and Their Transducing Properties"; 1984; Gene vol. 28, pp. 29-35.
J. Karn et al., "Novel Bacteriophage λ Cloning Vector"; P.N.A.S. vol. 77, Sep. 1980; pp. 5172-5176.

Primary Examiner—Richard A. Schwartz
Assistant Examiner—S. L. Nolan

[57] ABSTRACT

Vectors are described that circumvent traditional DNA cloning and subcloning procedures, and that contain a unique DNA cartridge that permits both cloning of DNA directly into DNA sequences present within the cartridge, and in vivo removal and circularization of the cartridge thereby yielding an autonomously replicating structure. Because the DNA cartridge can include a wide variety of functional DNA sequences, the cloned DNA can be subjected to a plethora of molecular biological procedures without having to remove the cloned DNA from the cartridge thereby obviating the need to perform additional subcloning techniques. A particularly useful example of this type of vector is bacteriophage lambda containing the DNA cartridge.

8 Claims, 16 Drawing Sheets

RsaI
5'
GTACGCGCCCTGTAGCGGGCGCATTAAGCGCGGCGGGTGTGGTGGTTACGC
~5513
GCAGCGGTGACCGCTACACTTGCCAGCGCCCTAGCGCCCGCTCCTTTCGCT
TTCTTCCCTTCCTTTCTCGCCACGTTCGCCGGCTTTCCCCGTCAAGCTCT
AAATCGGGGGCTCCCTTTAGGGTTCCGATTTAGTGCTTTACGGCACCTCG
                                          Sau96I 5725
ACCCCCAAAAAAACTTGATTAGGGTGTGATGGTTCACGTAGTG|GGCCATCGCCC
                                         HinfI 5767
TGATAGACGGTTTTTCGCCCTTTGACGTTGGAGTCCACGTTCTTTAATAG
HinfI 5789 (site of nick by gene II protein^)
TGGACTCTTGTTCCAAACTGGAA|CAACACTCAACCCTATCTCGGTCTATT
CTTTTGATTTATAAGGGATTTTGCCGATTTCGGCCTATTGGTTAAAAAAT
GAGCTGATTTAACAAAATTTAACGCGAATTTTAACAAAATATTAACGTT
TACAATTTAAA 3'
DraI    ^5947

```
          Hinf I        *site of gene II nick      EcoRV  NdeI
5'  AGTCCACGTTCTTTAATAGTGGACTCTTGTTCCAAACTGGAAGATATCCA  3'
3'  GGTGCAAGAAATTATCACCTGAGAACAAGGTTTGACCCTTCTATAGGTAT  5'
```

FIG. 4

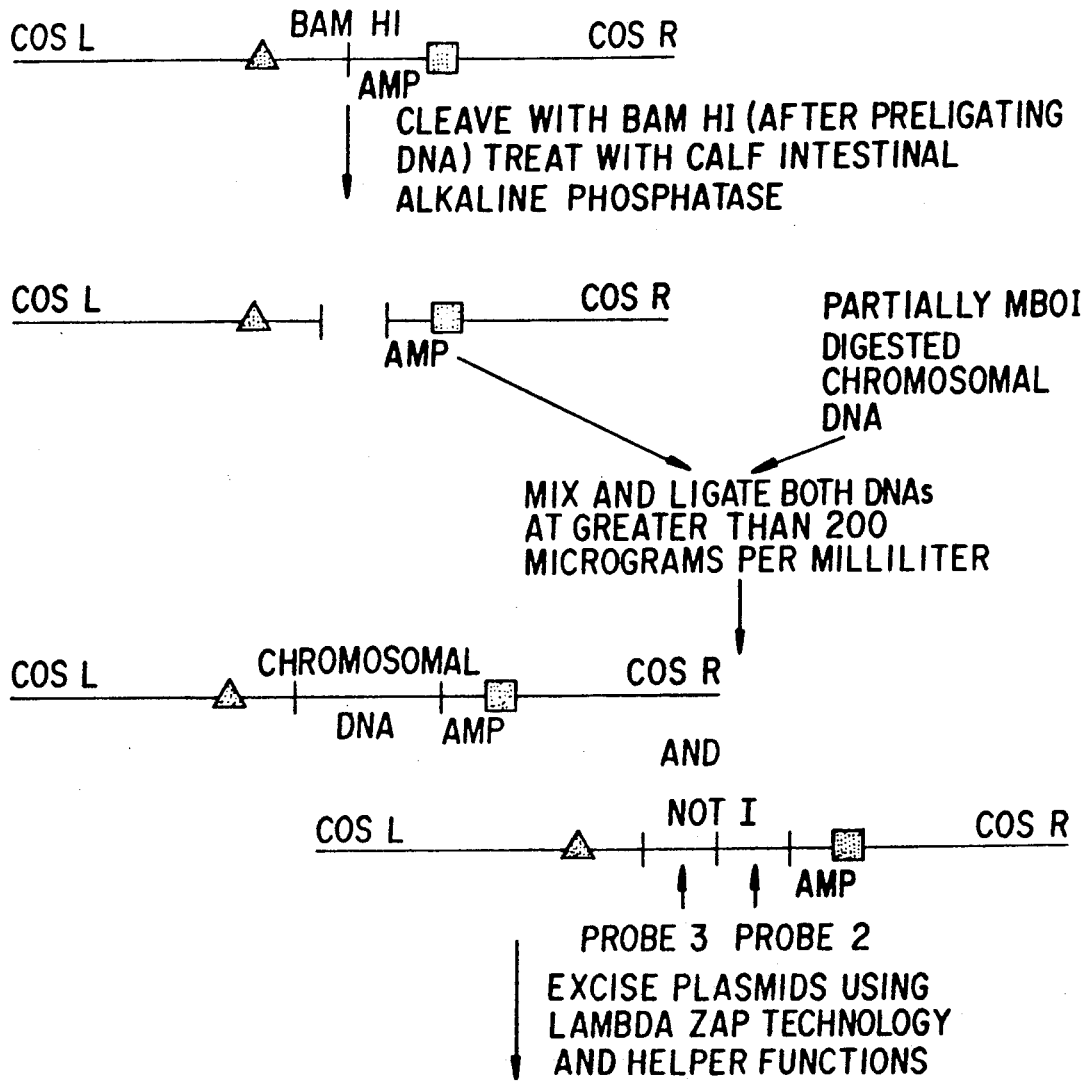
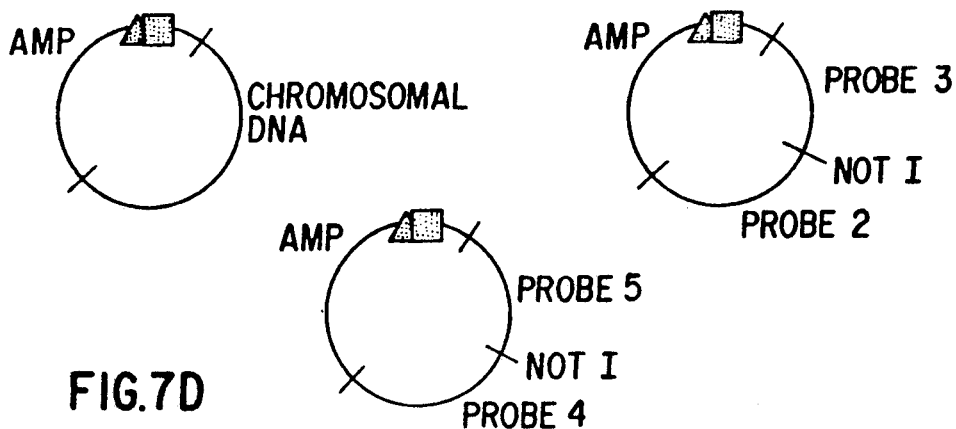
FIG.7D

DNA CLONING VECTORS WITH IN VIVO EXCISABLE PLASMIDS

This application is a continuation application based on application Ser. No. 002,441, filed on Jan. 12, 1987 now abandoned.

BACKGROUND OF THE INVENTION

Biotechnology centers on cloning and subcloning of genes, both of which are now routine procedures. The cloning step involves the creation of a gene library by fragmenting or restricting, using suitable restriction enzymes, the genome of an organism which comprises the starting material for the sought-after gene. These DNA fragments are then inserted into a suitable cloning vector, and the vector introduced into a host cell such as bacteria, yeast or like organism. Using appropriate detection and isolation techniques, host cells harboring vectors with a gene of interest can be identified, separated, and grown up in large amounts.

Regardless of the type of cloning vector employed, they are designed to facilitate creation of gene libraries by receiving large DNA fragments, and to be compatible with suitable host cells, as well as the materials and methods for growing up, isolating and detecting the vector in the host cells. Thus, particular cloning vectors generally have associated with them ancilliary biochemical materials and methods that are suited to the cloning process. A good example of this type of vector is bacteriophage lambda. Over the years its molecular biology has been elucidated, and consequently a number of vectors based on lambda, as well as support systems for isolating and propagating these vectors have been established.

Cloning a particular gene is generally just the initial step in isolating the gene in order to carry out specific biotechnical procedures utilizing the gene. Hence, it is often necessary to "subclone" the gene into a more functionally specific second vector. The latter are generally plasmids or derivatives or hybrids thereof. The process of subcloning consists of removing the DNA sequence from the initial cloning vector (i.e. lambda) with suitable restriction enzymes, and then inserting the DNA into a plasmid. Since the process of subcloning is time consuming, and technically arduous, the construction of high efficiency cloning vectors that would eliminate the subcloning step is a much sought after goal in biotechnology.

The ideal cloning vector would be transferable into bacteria and higher cells, and have the properties of both cloning and subcloning vectors. It can be imagined that this type of vector might consist of a subcloning vector integrated into the cloning vector, and that could be exised from the cloning vector to yield a plasmid. DNA could then be cloned directly into the subcloning vector, and the latter propagated and selected along with the cloning vector. Assuming that a method for excising and circularizing the subcloning vector from the cloning vector could be developed, the end result would be a vector that could be propagated, detected, and isolated using standard cloning vector techniques, yet bypass having to transfer DNA in a separate step into a subcloning vector, by excising and circularizing the subcloning vector.

It may be possible to generate the ideal cloning vector by manipulating particular DNA origins of replication. A common feature generally shared by cloning vectors is the presence of one or more DNA origins of replication. The latter allows for replication of the vector either autonomously, or concomitantly with host cell chromosomal DNA. Research efforts over the past several years have yielded information concerning nucleotide sequences that comprise origins of replication of different organisms. Further, work aimed at establishing which nucleotides in the origin are necessary for DNA synthesis has led to the realization that origins of replication, in at least some organisms, have distinct functional nucleotide domains. For instance, Dotto, et al in Journal of Molecular Biology (1984) Vol. 172, p. 507-521 have shown that the DNA origin of replication in filamentous single-stranded DNA bacteriophages comprises nucleotide sequences responsible for both initiating and terminating DNA synthesis. Thus, it may be possible to create the ideal vector consisting of a cloning vector, such as lambda, containing the initiator and terminator regions separated by intervening DNA. The intervening DNA could have numerous functions, including acting as a region into which to clone DNA. If conditions could be established whereby the initiator-terminator regions with accompanying intervening DNA could be excised from lambda with rejoining of the initiator-terminator regions, the end result would be a vector having the properties of a cloning vector (i.e. lambda), and an excisable plasmid (initiator-terminator regions and intervening DNA).

Although there exists a variety of DNA cloning techniques and vectors, there is a demand for cloning vehicles that facilitate a determination of the relative positions of DNA sequences along large stretches of DNA. For instance, it is generally difficult, or impossible to incorporate more than 50 kilobases into the bacteriophage vector, lambda. The latter is perhaps the most widely used and convenient vector for cloning large DNA fragments, because of the high efficiency with which lambda can be made to introduce genes into bacterial cells. Consequently this has led to the development of what is known as "chromosome walking" which involves isolating one recombinant phage or other cloning vehicle, particularly cosmids, and using it to isolate other recombinant vectors that contain overlapping DNA sequences. The technique relies on isolating a probe that can be used to identify a segment of DNA that is common to both a first and a second recombinant vector wherein the second recombinant contains additional and overlapping genetic information. The second recombinant can then be used to screen for a third recombinant containing information common to the second and third recombinants, and this procedure repeated to yield overlapping cloned gene segments. Unfortunately, however, "chromosome walking" is extremely time consuming and technically very demanding. In part, this is because present cloning systems do not facilitate cloning large segments of DNA. Thus a cloning vehicle that permits a determination of the relative positions of DNA sequences along large stretches of DNA is sorely needed.

C. M13 geneII protein recognizes the signal for termination of DNA synthesis and cleaves the DNA strand at the M13 recognition site.

D. M13 geneII protein converts the displaced strand of cDNA into a closed circular plasmid as the strand is cleared.

FIG. 2 shows the nucleotide sequence of the origin of replication of the bacteriophage, fl. This sequence is found in the fl origin of replication in the bacteriophage fl and pEMBL8. The nicking site of gene II is indicated and all map numbers are derived from the fl phage sequence (Deck, E. and Zink B, 1981, Gene, Vol. 18, pgs. 35–58). The upper box outlines the sequences required for terminator activity, while the lower box depicts those sequences required for initiator activity.

Figure 3A:
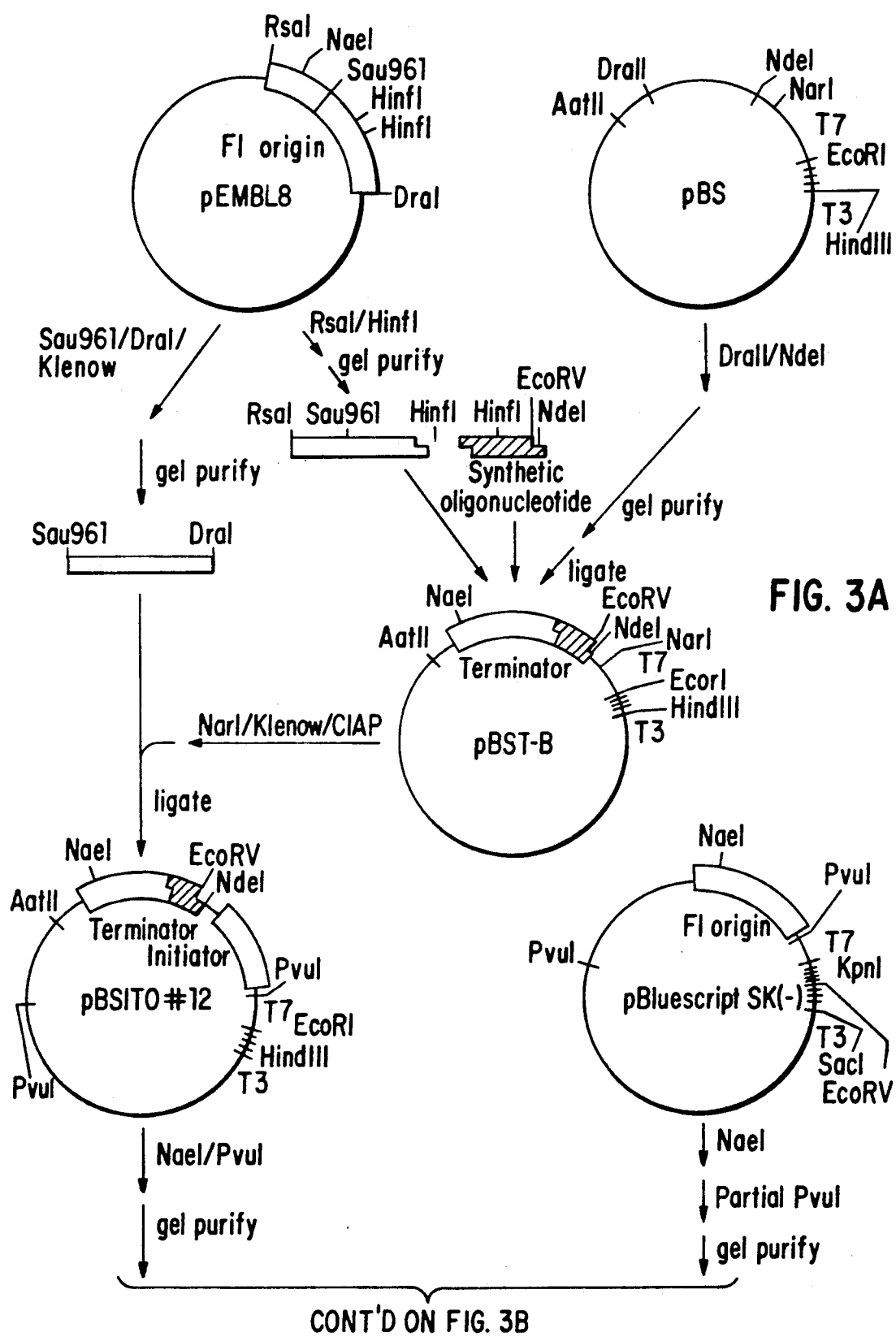
Figure 3B:
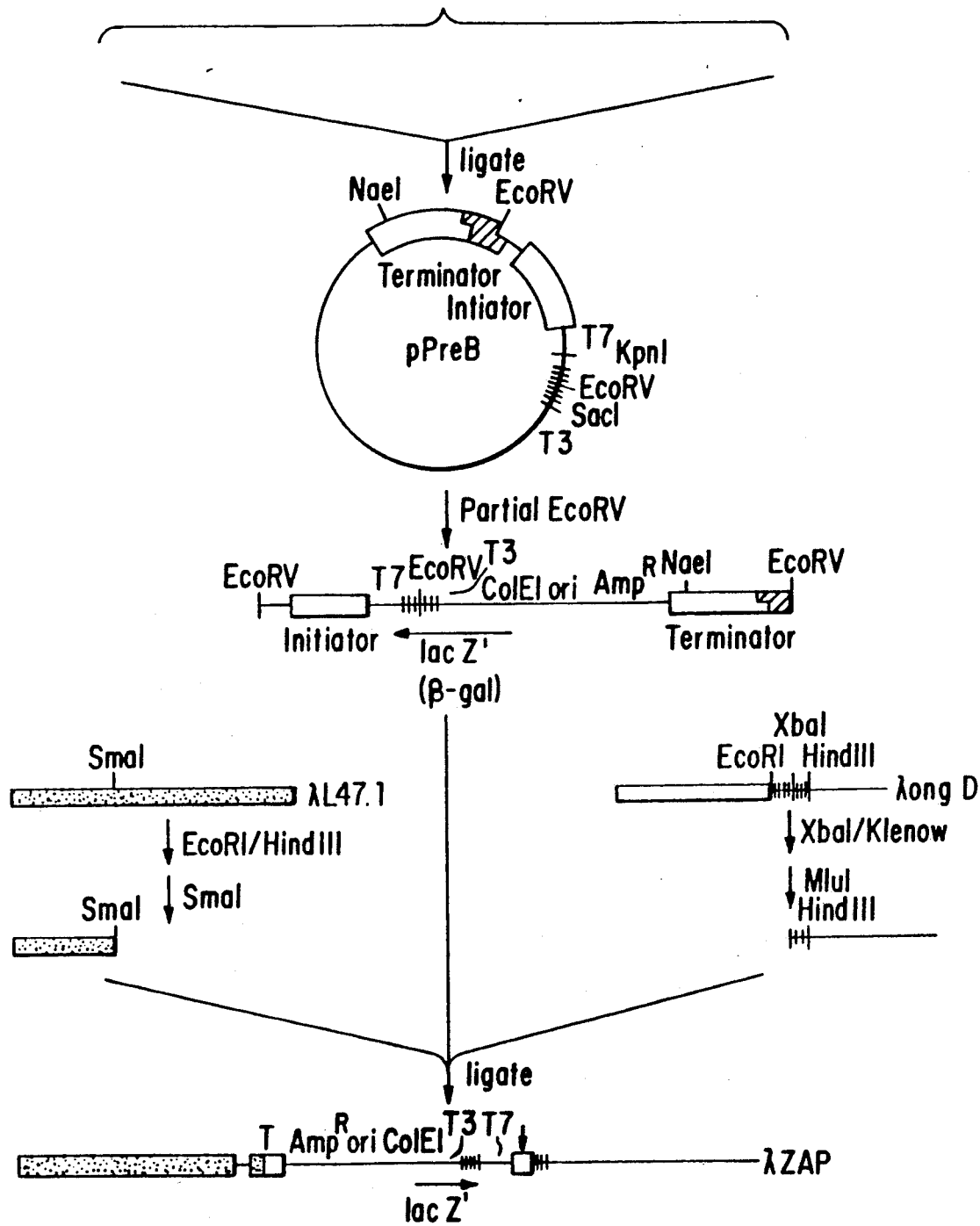

FIG. 3 depicts the isolation procedure wherein the initiator and terminator fragments are separately obtained, procedures wherein these fragments are cloned into suitable vectors, and their association with polylinker sites, T7-T3 RNA polymerase promoters, and a portion of the gene encoding beta-galacotasidase. The Figure also depicts the procedure for the generation of the separate initiator-terminator cartridge and its insertion into bacteriophage lambda to produce the vector lambda ZAP. The orientation of the initiator region is shown by the position of the arrow.

FIG. 4 depicts the sequence of the synthetic oligonucleotides used in part to construct a terminator region lacking initiator activity.

Figure 5:
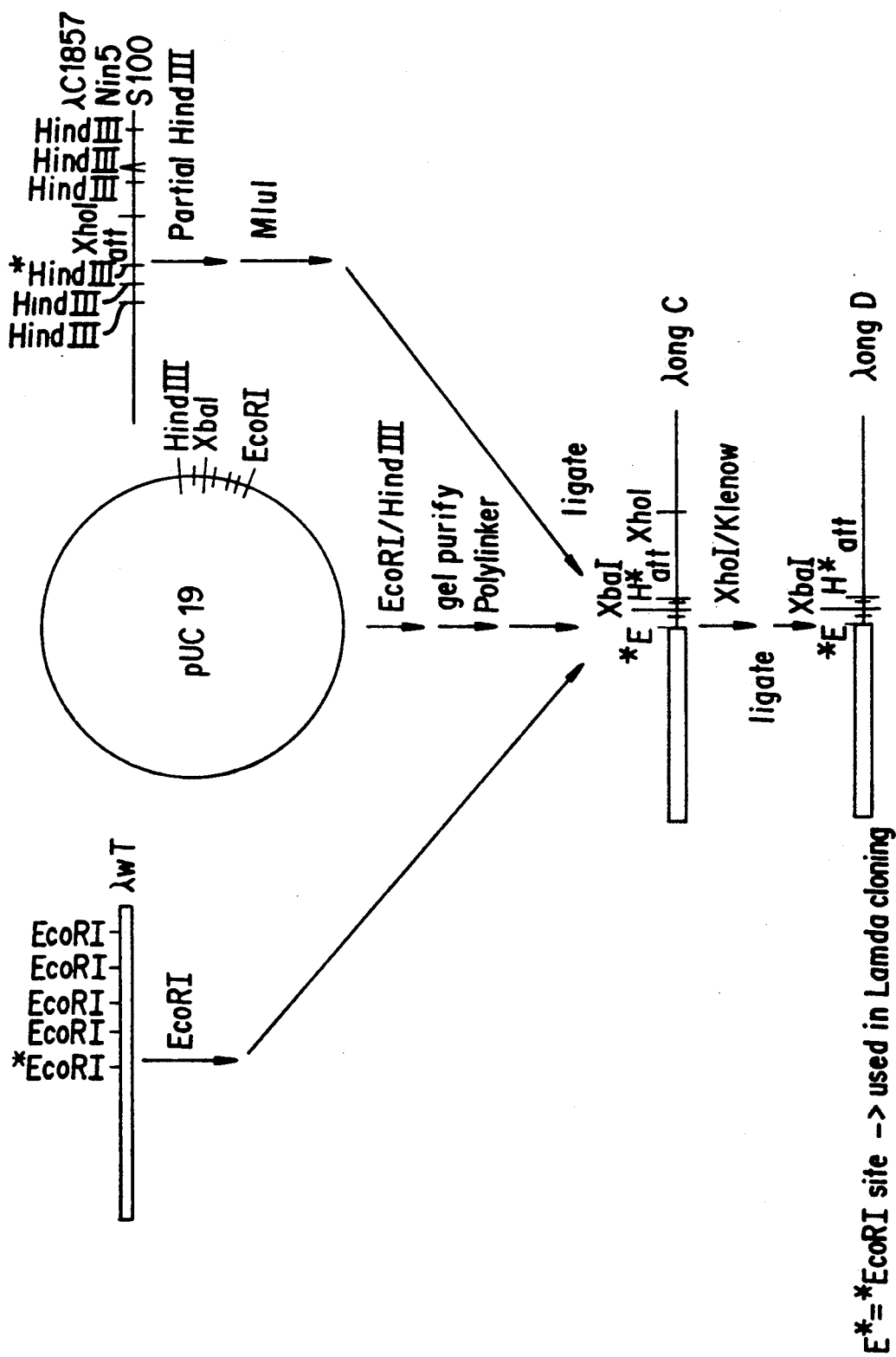

FIG. 5 depicts the scheme for generating the lambda vector, lambda Long D.

Figure 6:
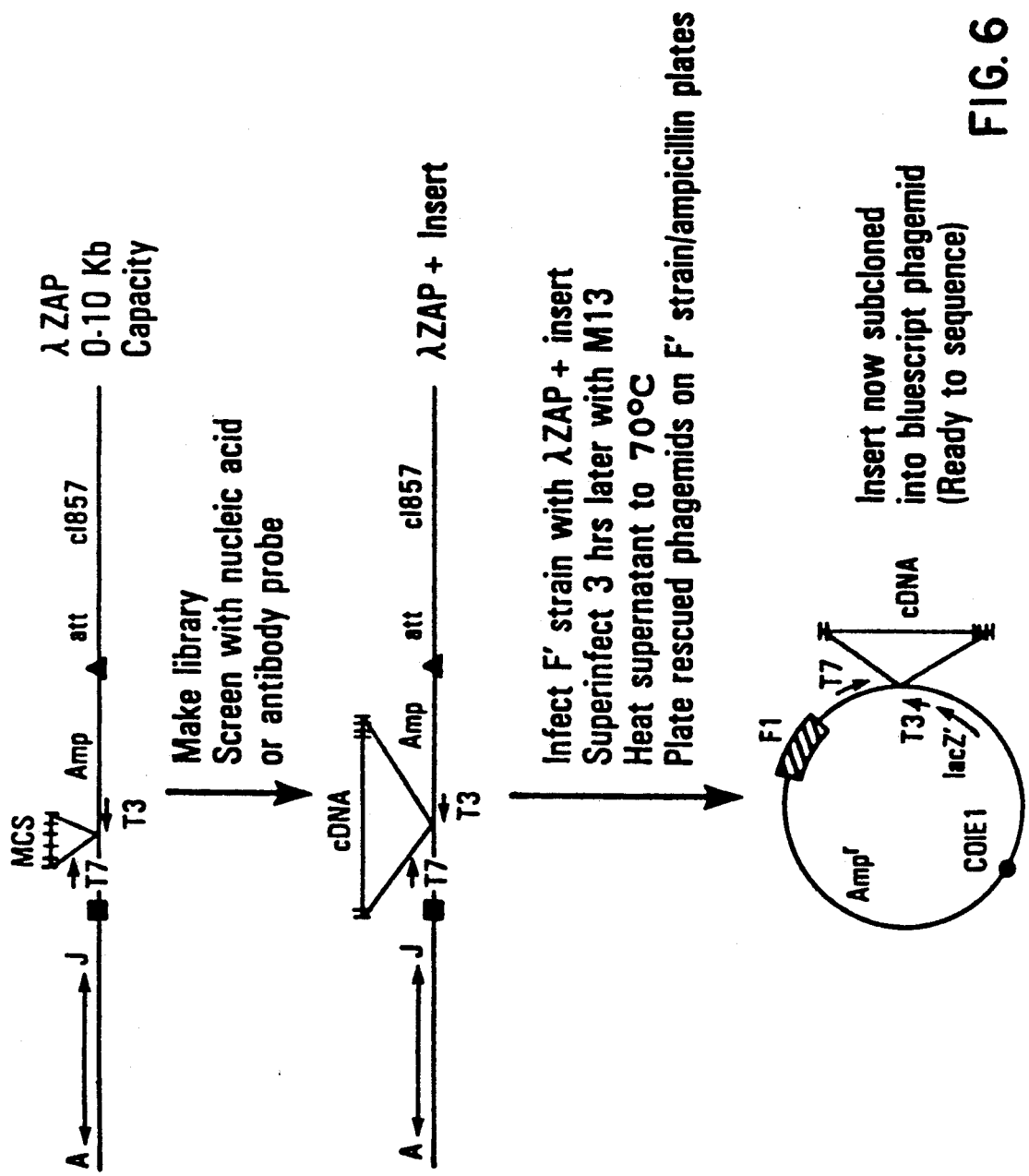

FIG. 6 shows a general scheme for excision of a plasmid from lambda ZAP. The M13 helper phage supplies trans-acting proteins which recognize two separate signals positioned within the lambda ZAP arms. The two signals were derived from two overlapping portions of an fl (M13) origin of replication and are termed initiator, ($\square$) which denotes the signal for initiation of DNA synthesis and terminator ($\Delta$), which denotes the signal for termination of DNA synthesis of a new DNA strand, the displaced strand is circularized to form the pBluescript SK (M13-) plasmid containing the cloned insert. Since pBluescript SK (M13-) contains the signals for packaging as a M13 filamentous phage, the circularized plasmid can be packaged and excreted from the cell. In this way pBluescript plasmids are recovered by infecting an F' strain and plating on Ampicillin plates.

Figure 7A:
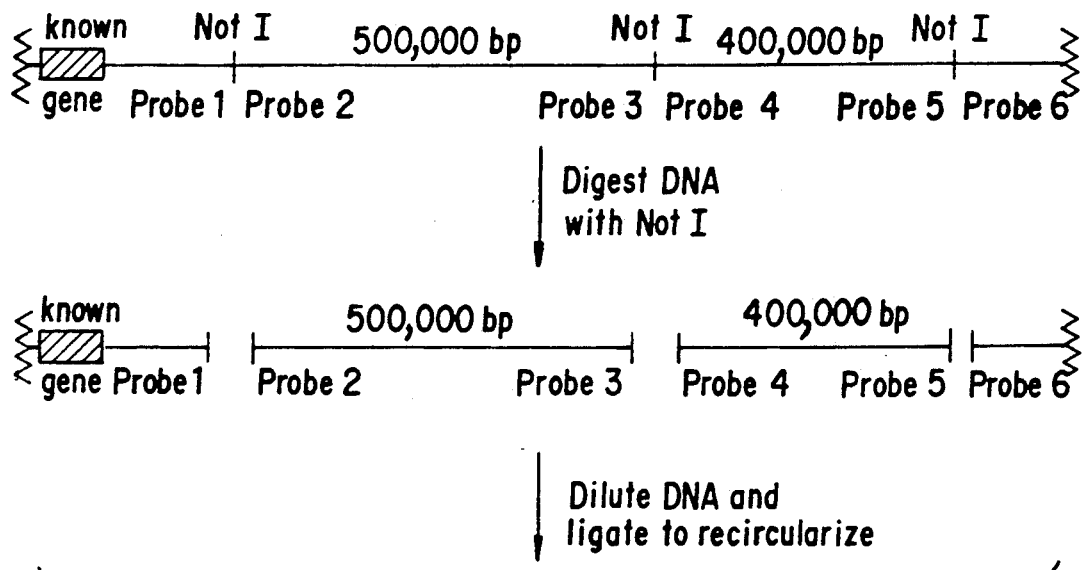
Figure 7B:
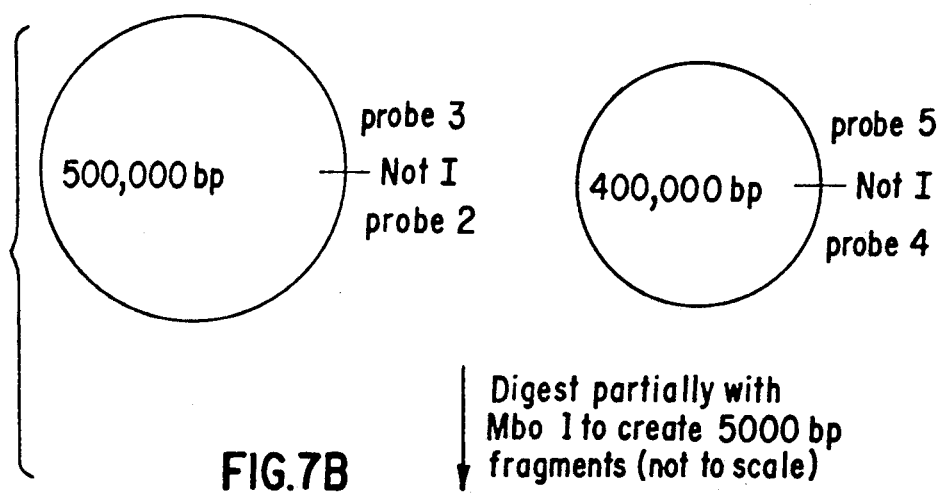

FIG. 7A-7B show the procedures for constructing the jumping library.

FIG. 8A-8F describes the procedure for constructing the junction library.

SUMMARY OF THE INVENTION

Vectors are described, as well as methods of producing them, that are useful for circumventing standard DNA cloning and subcloning procedures, and that can be advantageously employed to map large stretches of DNA.

These vectors are premised on the hithertofor unrecognized significance of certain facets of DNA replication, specifically that origins of replication consist of DNA sequences responsible for initiating as well as terminating DNA synthesis, and moreover, that these sequences can be independently isolated and cloned in a form that retains their respective activities. This finding has led to the production of DNA cartridges consisting of initiator and terminator regions separated by intervening stretches of DNA. The cartridges are insertable into cloning vehicles that are used to clone and subclone DNA. The latter is achieved in the presence of suitable proteins that effect the simultaneous synthesis of DNA corresponding to a cartridge of DNA, and the displacement and circularization of this cartridge of DNA as a single stranded molecule. Circularization causes a rejoining of the portions of the initiator and terminator regions thereby yielding a plasmid containing the intervening stretches of DNA.

The vectors consist of basically three classes of DNA; cloning vehicle DNA; initiator and terminator DNA derived from a DNA origin of replication; and DNA that is situated between the initiator and terminator DNAs. In a preferred embodiment of the invention, cloning vehicle DNA is bacteriophage lambda DNA modified so as to receive initiator and terminator DNA regions from a second bacteriophage, particularly filamentous *Escherichia coli* single-strand bacteriophages such as, fd, fl , and M13. Also other bacteriophages can be used, particularly $\phi$X174, IKE and G phage. The DNA situated between the initiator and terminator regions can consist of a variety of functional sequences, particularly restriction sites suitable for cloning DNA between the initiator and terminator regions, as well as other functional sequences such as cell or colony selectable markers, RNA polymerase promoters, etc.

The procedures for constructing the vectors described herein consist of isolating a DNA origin of replication and separating it into its component initiator and terminator regions using suitable DNA recombinant techniques. The initiator and terminator regions are manipulated to yield a vector having the regions separated by a stretch of intervening DNA, and bounded by unique restriction sites that allow for the excision of the terminator and initiator regions with intervening DNA. The presence of unique restriction sites bounding the initiator and terminator regions permits the ready excision of the initiator and terminator DNA with associated intervening DNA, thereby producing a vector transferable DNA cartridge. The latter can be ligated into various cloning vectors, and particularly into bacteriophage lambda. Lambda vectors can be constructed to accommodate the DNA cartridge, and about 20 kilobases of cloned DNA.

By cloning a DNA sequence into a restriction site located between the initiator and terminator regions, it is possible to avoid the procedure of subcloning by supplying suitable proteins that realize nicking, circularizing and cutting of displaced DNA comprising the initiator and terminator regions and intervening DNA. The resulting circularizing DNA is the replicative equivalent of functional subcloning plasmids. Also, because the terminator region enables the circularized DNA to be "packaged" and secreted from the host cell, the DNA can be recovered from infected cells using standard techniques, and processed for a variety of purposes and/or used to transform new host cells.

DETAILED DESCRIPTION OF THE INVENTION

The present invention describes materials and methods that considerably facilitate cloning and subcloning of DNA by essentially eliminating the traditional methods for performing these procedures. Moreover, as will become apparent below, the instant invention greatly facilitates mapping large stretches of DNA. While the invention described herein will be elucidated as applied to a particular cloning vehicle, bacteriophage lambda, it will be understood by those skilled in the art that the materials and methods described herein can be applied to other cloning vehicles with similar results. This is so because a significant aspect of the instant invention is a DNA cartridge that is readily employed with many types of cloning vehicles including plasmids, cosmids, viruses, and genetic combinations of these. A number of such cloning vehicles are shown by Colowick S. P. and Kaplan, N. O. in Methods of Enzymology, Volume 1, part C (eds. R. Wu, L. Grossman, and K. Moldave) Academic Press, Inc. New York. Others are described by Maniatis, T. et al in Molecular Cloning: A Laboratory Manual, Cold Spring Harbor Laboratory, Cold Spring Harbor (1982).

Lastly, it will be understood that the term plasmid is being used to refer to autonomously replicating structures as is presently understood in the art, but which may contain DNA from viruses, or other organisms, as well as bacterial DNA. The term phagemid may also be used to connote these structures.

The invention described herein is premised on the phenomena that the origin of DNA replication in bacteriophages, particularly filamentous phage known to infect the bacterium *Escherichia coli*, such as the bacteriophages fd, f1, M13, and Ike, G, and $\phi$X174 phage, is responsible for both initiating and terminating DNA synthesis. By separating the initiation and termination regions of the origin of replication, a DNA cartridge was constructed consisting of initiation and termination regions separated by an intervening region of DNA having DNA sequences desirable for performing various biotechnical manipulations. In the presence of suitable "helper" proteins circular DNA is produced that encompasses the parts of the original initiator-terminator regions and intervening DNA. The instant invention is understood by separately considering its component procedural aspects. These are, first derivation of a DNA cartridge having initiator and terminator regions; second, subcloning procedures using the initiator-terminator cartridge; third, considerations regarding the integration of the initiator-terminator cartridge in lambda; and fourth, using vectors containing initiator-terminator cartridges.

I

DERIVATION OF AN UNITIATOR-TERMINATOR CARTRIDGE

The origin of replication of filamentous single-stranded DNA bacteriophages was separated into the two functional DNA sequences corresponding to the initiator and terminator sequences, respectively. In order to separate the initiator and terminator regions, it is, of course, necessary to identify those DNA regions that exhibit the corresponding activities. A number of origins of replication are known to those skilled in the art, and many have already been isolated and cloned. For certain origins of replication the initiation and termination regions overlap, while for others they do not. (See, for example, Chang and Cohen, Construction and Characterization of Amplifiable Multi-copy DNA Cloning Vehicles Derived from the P15A Cryptic Mini Plasmid, Journal of Bacteriology, Vol. 134, pp. 1141-1156, 1978. Using deletion and insertion analysis techniques, also well known to those skilled in the art (Dotto, et al., above), it is possible to identify the sequences responsible for initation and termination. These regions can be fragmented using suitable molecular methods, and the initiator and terminator regions isolated using standard techniques, and then cloned and propagated in a suitable vector. These procedures enable one to derive a vector carrying both the initiator and terminator regions but which are no longer contiguous.

While there are a variety of procedures suitable for separating and cloning the initiator and terminator regions from the origin of replication, it is anticipated that most often either one of two procedures may be followed. In those instances where the initiator and terminator regions do not overlap, and exhibit unique restriction sites at the boundary of the initiator and terminator sequences, it is a fairly simple task to separate the regions by restriction enzyme digestion, and then isolate and clone them into a suitable vector. Several procedures are available for realizing this depending upon the nature of the restriction sites, but they generally have in common production of initiator and terminator regions with ligatable termini. For example, a number of restriction enzymes are well known to cleave DNA at sites to produce DNA fragments with cohesive ends, which can be joined to other DNA fragments with similar cohesive ends. If such sites are exhibited by a particular origin of replication, it will be possible to obtain initiator and terminator regions having cohesive ends and to insert them into a vector treated with similar restriction sites, thereby matching cohesive ends. Alternatively, other restriction enzymes that produce blunt end DNA fragments may be utilized to generate the initiator and terminator regions. Both blunt and cohesive ends can be joined with a suitable (i.e. T4) ligase enzyme as described by Maniatis et al, above.

In addition to the above two approaches, there are available a truly bewildering combination of procedures for joining DNA fragments that have cohesive ends to DNA fragments having blunt ends. In this instance, generally, the cohesive ends are "filled in" and then ligated to the blunt end, using the Klenow fragment and suitable nucleotides. Cohesive termini may also be introduced by enzymatically removing or adding nucleotides from the ends of the fragments. Also, it will be appreciated that synthetic DNA "linkers" or "adaptors" can be generated or obtained commercially and employed to produce cohesive ends. Again, virtually all of these procedures are well known to those skilled in the art and are succinctly described in Glover in DNA Cloning, Vol. 2, A Practical Approach (1985, IRL Press, Oxford, Washington, D.C.) and Maniatis et al., above.

The procedures concerning the use of restriction enzymes, their nucleotide specifities, cofactor requirements, etc. are also known to those skilled in the art, or are shown in the prior art and readily available. A description of these may be found in Maniatis et al above, and Glover in DNA Cloning, Vol. 2, A Practical Approach (1985, IRL Press, Oxford, Washington, D.C.). In the event the DNA initiator and terminator regions are not discrete, but exhibit overlapping DNA sequences necessary for their respective functions, it is possible to separately identify and isolate part of either one or both regions so as to yield DNA fragments having discrete initiator or terminator activities, thereby reducing the possibility of isolating fragments having a mixture of activities. Again, using deletion and insertion techniques described by Dotto, et al above, overlapping regions of DNA can be identified and removed with suitable restriction enzymes. In some instances it will be desirable to replace the removed sections with a synthetic oligonucleotide which can facilitate subsequent insertion of the fragment into a vector. Particularly desirable for the latter procedure will be oligonucleotides with one or more restriction sites whereby they can be matched with a vector having similar restriction sites thereby facilitating ligation.

After the DNA fragments containing the initiator and terminator regions have been independently isolated, they are cloned into a suitable vector having restriction sites that permit their removal and subcloning, so as to permit the association of desirable DNA sequences between the initiator and terminator regions. A variety of procedures will be apparent to those skilled in the art whereby this can be achieved. To a large extent, however, determinative of whether a particular approach is taken, will be the nature of the DNA sequences that are sought to be positioned between the initiator and terminator regions. Since numerous vectors are available, or easily constructed, that exhibit poly-linkers, drug markers, etc., the initiator and terminator fragments can be cloned either directly or indirectly into a vector having the desirable intervening DNA sequences thereby producing a vector having the initiator and terminator fragments bounded by restriction sites and separated by an intervening stretch of DNA exhibiting poly-linkers, etc.

Since it is preferred that the initiator and terminator fragments, and intervening DNA be removable as a unit from the host vector, the restriction sites that bound the fragments should be infrequently present in the intervening DNA regions. If such sites are, however, present they should not be enzymatically digested under well defined reaction conditions, such that partial digestion occurs, thereby causing cleavage of the sites bounding the initiator and terminator fragments, but without cleaving the intervening DNA. Similarly, any restriction sites present in the intervening stretch of DNA such as those present in the poly-linker, etc., should be different, or functionally enzymatically distinguishable from those sites that bound the initiator and terminator fragments. This, of course, permits cloning of foreign DNA into a poly-linker site without possibly removing the initiator and terminator fragments.

The unit comprising the initiator and terminator sequences bounded by unique enzyme restriction sites, and enclosing technically useful DNA sequences, will hereinafter be referred to as the initiator-terminator cartridge. It will be appreciated that the size of the cartridge can vary considerably depending on the size of the intervening DNA, as well as the nature of the cloning vehicle into which it is inserted.

The instant invention describes the isolation of initiator and terminator regions from filamentous single stranded DNA viruses. However, this should not be construed as limiting the invention to such viruses as a source of the regions. It is particularly important to realize that since the DNA sequences of the regions are known, that each could be synthesized using known DNA synthesis techniques. Moreover, synthetic initiator-terminator regions having nucleotide sequences distinct from those found in the filamentous single stranded DNA viruses can be produced, and these regions can be expected to have significantly better initiator and/or terminator activity.

The initiator-terminator cartridge has many uses. For instance, it can be inserted into a variety of vectors and employed to construct gene libraries from either cDNA, or genomic DNA, whereby foreign DNA is cloned in between the initiator-terminator regions at a suitable restriction site. After the vector is inserted into a suitable microbial host cell by one of many techniques well known to those familiar with the field of molecular biology (i.e. transformation, infection, electroporation, etc.) cells harboring vectors with particular cloned genes can be identified using immunochemical, or DNA or RNA probe technology, or combinations of these technologies. The cell can be isolated and propagated to provide a source of vector containing the initiator-terminator cartridge. The latter can be excised, the DNA propagated in an appropriate manner (Maniatis et al above), and then isolated and subsequently used for expressing, sequencing, mapping, generating RNA or DNA probes, or in other ways utilizing the cloned DNA.

II

SUBCLONING USING THE INITIATOR-TERMINATOR CARTRIDGE

As mentioned above, subcloning is generally necessary to realize well defined hybridization probes, or to perform sequencing, mutagenesis, etc. Subcloning has traditionally required removing the genomic or cDNA inserts from the vector that they were initially cloned into, and then transferring the DNA inserts into another, second vector, usually a plasmid that has the requisite desirable properties. An appealing feature of the initiator-terminator cartridge is that under certain conditions DNA molecules comprising the initiator-terminator and intervening DNA sequences are circularizable. Circularization essentially equates to "subcloning", as the result is a plasmid-like structure. Thus the need to subclone DNA is an independent step is eliminated.

Circularization can be readily achieved for initiator-terminator cartridges having initiator and terminator fragments derived from filamentous bacteriophages such as $\phi$X174, f1, fd, M13, IKE and G phage by providing the gene II product or functional equivalents produced by the appropriate phages. It will be understood that the term "gene II product" is used in a functional sense to mean a protein or proteins responsible for the stated event. The latter has a twofold function: first, it nicks one of the two DNA strands of the initiator DNA, thereby commencing DNA synthesis of DNA "down stream", or 3' of the nick site, and continuing through any DNA situated between the initiator and terminator regions displaying the old DNA strand, and terminates in the terminator sequences. Second, the displaced single-stranded cartridge DNA produced is both cleaved and circularized by the gene II product.

It is noteworthy that gene II products from a particular phage may or may not recognize initiator terminator sequences from different phages. However, gene II products from closely related phages such as f1, fd and M13 are anticipated to substitute for one another, whereas gene II products from $\phi$X174 G, and IKE are similarly expected to be enzymatically equivalent and cross recognize their respective initiator-terminator sequences.

Figure 1:
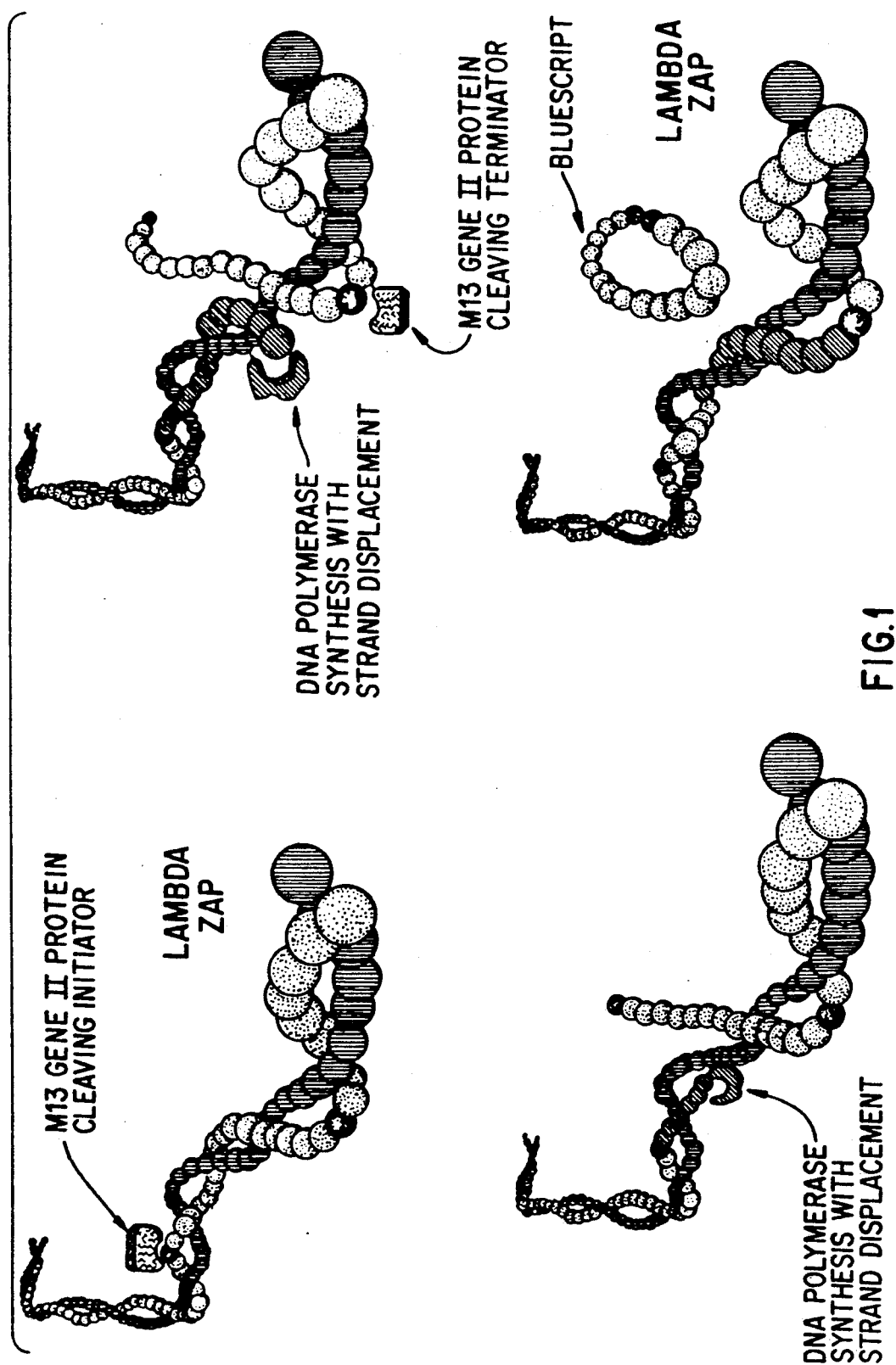
FIG. 1. Automatic Excision of cDNA's from Lambda ZAP to pBluescript SKM13-
  A. M13 geneII protein recognizes the signal for the start of DNA synthesis and cleaves the DNA strand at the M13 recognition site.
  B. DNA polymerase present in the host cell synthesizes a new strand, displacing an existing strand.

It will be appreciated by those skilled in the art that circularization results whenever the gene II product is present and reacts with the initiator-terminator cartridge. This can be achieved by co-infecting a microbial cell with one of the above-described appropriate bacteriophages and a cloning vehicle with the initiator-terminator cartridge. In this instance the bacteriophage produces the gene II product, or equivalent protein(s) which recognizes and reacts with the initiator-terminator sequences causing DNA synthesis and circularization of the strand displaced by DNA synthesis. This is conceptionally represented in FIG. 1. While this is the preferred method of circularization, it is anticipated that a variety of other methods will also perform satisfactorily. For instance, gene II can be cloned directly into the cloning vehicle that carries the initiator-terminator cartridge. In this way a single vector will carry the initiator-terminator cartridge and supply the proteins necessary to circularize DNA molecules.

It will be appreciated that circularization results in rejoining the initiator-terminator regions. By selecting intervening DNA having replication and selection functions compatible with a suitable host cell it is possible to generate circular double stranded DNA molecules that are functionally the equivalent of a plasmid.

III

LAMDBA CONTAINING INITIATOR-TERMINATOR CARTRIGGES

While it is anticipated that the initiator-terminator DNA cartridge can be inserted into a variety of cloning vehicles, the preferred embodiment of the invention is the insertion of the cartridge into a bacteriophage lambda vector. Bacteriophage lambda is known to contain about 50 genes, although only about 60% of these are necessary for lambda's growth and plaque forming ability. It will be appreciated that any means whereby lambda is reduced in size without affecting its growth cycle or packaging functions permits large stretches of intervening DNA to be situated between the initiator and terminator regions. Lambda phage vectors are generally thought of as comprising three parts; a left arm, a stuffer fragment, and a right arm. The left arm consists of approximately 20 kilobases of DNA and includes the head and tail genes. The right arm comprises the nucleotides ranging from ATT through the cosR site, although shorter versions lacking ATT can be constructed.

The "stuffer" portion of the virus comprises the middle one-third of the genome, and is nonessential for viral growth, and thus it is most often replaced with foreign DNA. Since the viability of lambda is known to drop off significantly when DNA longer than about 105% or shorter than about 78% of the wild-type genome is packaged, if one wishes to use a initiator-terminator cartridge having short stretches of intervening DNA, or to clone short sections of DNA into a poly-linker site, then it is anticipated that less of the viral genome will be deleted, whereas the opposite is true for larger DNA sequences.

In addition to omitting the stuffer fragment, the left and right arms can be reduced in size without affecting lambdas growth or packaging functions. This permits cloning of large DNA inserts into initiator-terminator cartridges having poly-linker sites. By omitting the stuffer fragment and reducing the size of the left and right arms, lambda vectors can be generated that incorporate a initiator-terminator cartridge capable of receiving DNA inserts about 10 kilobases or longer in length in a poly-linker region of the cartridge. One particularly useful lambda vector, termed ZAP, has DNA sequences corresponding to T7 and T3 RNA polymerase promoters, a polylinker, ColEl origin of replication, a portion of the LAC-Z and the ampicillin genes.

As alluded to above, the initiator-terminator cartridge can be inserted into a number of cloning vectors, including plasmids, cosmids, viral vectors or hybrids thereof. The general requirement is that the initiator-terminator cartridge have ligatable termini thereby enabling it to be inserted into a non-essential region of the vector. An example of a useful hybrid is a "shuttle" vector. The latter vectors are capable of replicating in both procaryotes and eucaryotes, as described by Struhl, Stinchcomb, Scherer, and Davis in *Proceedings of the National Academy of Sciences*, page 1035, Vol. 76, 1979. Moreover, a general description of expression vectors and methods of using and isolating the same are taught by Glover in *DNA Cloning*, Vol. 2, *A Practical Approach* (1985, IRL Press, Oxford, Washington, D.C.).

IV

GENOMIC MAPPING WITH LAMBDA CONTAINING INITIATOR-TERMINATOR CARTRIDGES

There are a wide variety of uses for vectors, particularly bacteriophage lambda vectors, that carry the initiator-terminator cartridge. Aside from the advantages that they offer in subcloning DNA, they can be favorably employed in the construction of clones useful in locating or mapping the position of DNA sequences along chromosomes relative to one another. This can be achieved by establishing what will hereinafter be referred to as "jumping" and "junction" DNA libraries. (See Collins, F. S. and Weissman S. M. proceedings of National Academy of Science, Vol. 81, p. 6812 (1984))

Reference to the following diagram will facilitate understanding the production and use of jumping and junction libraries. The diagram illustrates a stretch DNA.

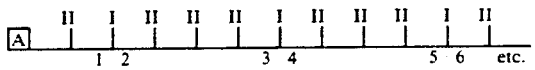

"A" refers to an identifiable DNA sequence, for which there is a preexisting method for detection. 1:2, 3:4, 5:6, etc., refer to DNA sequences separated by the same restriction site, the latter is denoted by "I". "II" denotes one or more restriction sites that separate the DNA sequences 2:3, 4:5, etc. The goal is to identify the linear positions of the sequences relative to "A". Because the distance from 2 to 3, 4 to 5, etc. is large (about 500 kilobases), it has hithertofor not been possible to order the positions of such widely separated sequences by current technology without considerable technical difficulty.

A jumping library is constructed which involves cleavage at the I site to yield fragments, termed I fragments having sequences 2:3, 4:5, etc., at the remote ends of the fragments. The fragments are circularized by ligation under suitable conditions that favor circularization over multimer formation. It is important to note that circularization occurs at and thereby effects the joining of remote sequences 2:3, 4:5, etc. The circular DNA molecules are then reacted with one or more enzymes that cleave at the II sites thereby producing an array of fragments. Since cleavage does not occur between sequences 2:3, 4:5, etc., some of these fragments, termed II fragments, will consist of DNA sequences (i.e., 2:3, 4:5) that were initially located at opposite ends of the I fragments.

The II fragments are inserted into a lambda ZAP-like vector after complete or partial digestion, and the latter is generated as described above. This vector does not contain the T3 or T7 promoters, but does exhibit at least one selectable marker. The gene encoding ampicillin resistance will perform satisfactorily. The vector is cleaved between the initiator and terminator regions at a site remote from the ampicillin gene, particular usable sites are BAM HI (and XhoI). If insertion at the latter site is desired from the procedure of Eugene R. Zabanorsky and Rando Lallorkmets as described in Gene, Vol. 42 (86) 119-123 is followed. If the BAM HI site is used the vector is treated with alkaline phosphatase as described by Maniatis et al, above, followed by ligation of the II framgments into the vector at a concentration of about 200 micrograms/per milliliter. The procedures for packaging, infecting, growing lambda, and for generating circular plasmids from the lambda ZAP-like vectors using helper proteins as described in the preceding example, are followed. This results in plasmids harboring the II fragments. Some of these vectors will have II fragments with the sequences 2:3, 4:5, etc., and others will not.

In order to identify those vectors containing II fragments with the sequences 2:3, 4:5, etc., and to be able to make probes to these sequences, the vectors are cleaved with the same enzyme, or one having the same nucleotide specificity, used to cleave at the I sites, and a DNA cartridge is then inserted and ligated between the sequences 2:3, 4:5. It is important to note that only those vectors containing II fragments with these sequences (i.e., the I sites) will be cleaved, and thus capable of receiving the cartridge. The cartridge consists of RNA polymerase promoter regions, two such suitable promoters are the bacteriophage promoters T3 and T7. It also has a selectable marker distinct from that already present in the vector. Kanamycin is an example of a suitable selectable marker. The promoters are oriented to yield RNA transcripts of the sequences 2 or 3 in a vector with these sequences, or 4 or 5 in a second vector, and so on for other vectors with other sequences. Because the cartridge contains a selectable marker, vectors containing sequences 2:3, 4:5, etc., have two selectable markers, and can be isolated in double drug selection media after transformation of the vector into a suitable host cell. In contrast vectors that lack the 2:3, 4:5, etc., DNA sequences are not susceptible to cleavage, and therefore do not receive the DNA cartridge. While these vectors have a single drug selectable marker, cell transformats that contain these vectors do not survive in double selection media.

The identification of cells harboring lambda ZAP-like derived plasmids containing those DNA sequences initially located at the opposite ends of the I fragments, and containing bacteriophage promoters for generating probes to these sequences, represents the completion of the production of the jumping library.

The production of a junction library is constructed similarly to the jumping library with the exception that the initial cleavage event of the DNA shown in the above diagram involves producing II fragments. It is important to be aware that cleavage at II sites occurs between DNA sequences 3:4, 5:6, etc., but not between sequences 2:3, 4:5, etc. Thus, the initial step yields what are termed junction fragments. The latter are inserted in the same or similar lambda ZAP like vectors used for making the jumping library. The remaining steps for producing the junction library are generally the same or similar to those producing the jumping library. The end result are cells harboring lambda ZAP-like vectors derived plasmids containing junction sequences separated by a selectable marker and bacteriophage promoters.

Using the jumping and junction libraries, it is possible to order DNA sequences that are separated over large distances along a stretch of DNA. For instance, it will be apparent that by using conventional "walking" techniques it is possible to identify sequences and to generate probes to sequences 1 and 2. The availability of a probe to sequence 2 permits plasmids to be identified from the jumping library that carry sequence 2, and additionally sequence 3. In this manner, it is possible to identify DNA sequences located at opposite ends of large molecular weight DNA fragments (I fragments). However, it is further apparent that the existence of a jumping library alone does not permit the continued detection of other plasmids with additional sequences located at the ends of other I fragments so as to decipher their relative order. For instance, it is not possible to show that sequences corresponding to sequences 4 and 5 occupy the same fragment nor their position relative to sequences 2 or 3. This can be achieved, however, by probing the junction library using the 3 sequence probe. The latter will identify cells harboring vectors with the sequences 3 and 4. Using RNA polymerase generated probes to sequence 4 the jumping library can again be probed to identify cells with vectors harboring sequences 4 and 5. Thus, by alternatively probing the jumping and junction library in this manner, the relative order of the sequences can be determined.

It will be apparent to those skilled in the art that there are numerous materials and methods that can be suitably employed to effect the ultimate goals of the subject invention. Thus, the following examples are to be considered illustrative and not restrictive of the instant invention.

EXAMPLE I

Isolation of Terminator and Initiator Fragments from the Filamentous Single-stranded DNA Bacteriophage, f1

The first step in the construction of a initiator-terminator DNA cartridge, is the isolation of initiator and terminator fragments from a suitable bacteriophage. This was realized using the bacteriophage f1. FIG. 2 shows the f1 origin of replication, specifically, that it is contained within a 434 base pair region of DNA. The sequence is bounded by two naturally occurring restriction sites, Rsa I (position 5513) and Dra I (position 5947). Moreover, FIG. 2 shows that the initiator and terminator nucleotides overlap. The f1 intergenic region has previously been isolated by Dotto, above, and cloned into a vector, pEMBL8. The latter is thus useful for isolating initiator-terminator sequences, and is obtainable from the American Type Culture Collection.

FIG. 3 shows in schematic form the isolation procedure. The initiator fragment was isolated from pEMBL8 by treating the plasmid with the restriction enzymes Sau 96I and Dra I. These enzymes recognize the naturally occurring restriction sites at positions 5725 and 5947, respectively. 10 to 50 ug of restriction digested plasmid DNA was electrophoresed on a 0.8 to 1.4% agarose gel in 1×E Buffer [50 mM Tris (Acetate)

pH8: 2 mM EDTA, pH8] until the DNA fragments were completely separated. DNA bands were visualized by ethidium bromide staining of the gel 0.5 ug ethidium bromide/ml), and the fragments identified by comparison to DNA size markers loaded in adjacent lanes of the gel. Next, the appropriate DNA band was cut from the gel, eluted by electrophoresis in autoclaved dialysis bags (MW cut off 10,000). The fragment was removed from the dialysis bag, pipetted into a 50 ml conical tube, and the DNA concentrated by extraction with isobutanol. It was then transferred to an eppendorf tube and twice extracted with distilled phenol and chloroform equilibrated with water followed by precipitation by adding two volumes of absolute ethanol and incubating overnight at −20 degrees Centigrade. DNA was pelleted by centrifugation at 12,000×g for 15 minutes. In order to determine the concentration of recovered DNA, the pelleted sample was resuspended in $T_{10}E_1$ buffer (10 mM Tris-HCl, pH7.5, 1 mM EDTA) and assayed by the ethidium spot assay as described by Maniatis et al above. Restriction enzymes were purchased from New England Biolabs, and the reaction conditions under which they were employed were those suggested by either the manufacturer, or as described by Maniatis, et al., above.

FIG. 3 also shows that the terminator fragment was isolated from pEMBL8 using the restriction enzymes Rsa I and Hinf I. The resulting fragment was purified, as described above, and corresponds to nucleotides 5513–5767 shown in FIG. 2. A synthetic oligonucleotide was ligated at the naturally occurring Hinf I site at position 5767 and extends to position 5809 within the fl sequence. FIG. 4 shows the oligonucleotide base sequence where position 5809 marks the end of the termination site. Eight nucleotide bases were added at this position to incorporate restriction sites for EcoRV and NdeI. This yielded an oligonucleotide of about 50 base pairs in length. The oligonucleotide was synthesized using an Applied Biosystems DNA synthesizer following the manufacturer's instructions.

EXAMPLE II

Cloning of the Initiator and Terminator Fragments

A plasmid, pBSITO #12, having the initiator and terminator fragments as inserts was constructed as shown in FIG. 3. The initial step involved the insertion of the terminator fragment, encompassing the Rsa I/-Hinf I fragment, ligated to the synthetic oligonucleotide, hereinafter referred to as the terminator fragment, into a plasmid, pBS, or pBluescribe, shown in FIG. 3. The synthetic oligonucleotide is shown in FIG. 4. A description of pBluescribe can be found in Stratagene Cloning Systems Manual, Stratagene Corporation, San Diego, Calif. The description of the nucleotide sequence of pBluescribe M13- is shown below:

```
   1 TCGCGCGTTT CGGTGATGAC GGTGAAAACC TCTGACACAT GCAGCTCCCG GAGACGGTGA
  61 CAGCTTGTCT GTAAGCGGAT GCCGGGAGCA GACAAGCCCG TGAGGGCGCG TCAGCGGGTG
 121 TTGGCGGGTG TCGGGGCTGG CTTAACTATG CGGCATCAGA GCAGATTGTA CTGAGAGTGC
 181 ACCATATGCG GTGTGAAATA CCGCACAGAT GCGTAAGGAG AAAATACCGC ATCAGGCGAC
 241 GCGCCCTGTA GCGGCGCATT AAGCGCGGCG GGTGTGGTGG TTACGCGCAG CGTGACCGCT
 301 ACACTTGCCA GCGCCCTAGC GCCCGCTCCT TTCGCTTTCT TCCCTTCCTT TCTCGCCACG
 361 TTCGCCGGCT TTCCCCGTCA AGCTCTAAAT CGGGGGCTCC CTTTAGGGTT CCGATTTAGT
 421 GCTTTACGGC ACCTCGACCC CAAAAAACTT GATTAGGGTG ATGGTTCACG TAGTGGGCCA
 481 TCGCCCTGAT AGACGGTTTT TCGCCCTTTG ACGTTGGAGT CCACGTTCTT TAATAGTGGA
 541 CTCTTGTTCC AAACTGGAAC AACACTCAAC CCTATCTCGG TCTATTCTTT TGATTTATAA
 601 GGGATTTTGC CGATTTCGGC CTATTGGTTA AAAAATGAGC TGATTTAACA AAAATTTAAC
 661 GCGAATTTTA ACAAAATATT AACGTTTACA ATTTCGCCAT TCGCCATTCA GGCTACGCAA
 721 CTGTTGGGAA GGGCGATCGG TGCGGGCCTC TTCGCTATTA CGCCAGCTGG CGAAGGGGGG
 781 ATGTGCTGCA AGGCGATTAA GTTGGGTAAC GCCAGGGTTT CCCAGTCAC GACGTTGTAA
 841 AACGACGGCC AGTGAATTGT AATACGACTC ACTATAGGGC GAATTCGAGC TCGGTACCCG
 901 GGGATCCTCT AGAGTCGACC TGCAGGCATG CAAGCTTTTG TTCCCTTTAG TGAGGGTTAA
 961 TTCCGAGCTT GGCGTAATCA TGGTCATAGC TGTTTCCTGT GTGAAATTGT TATCCGCTCA
1021 CAATTCCACA CAACATACGA GCCGGAAGCA TAAAGTGTAA AGCCTGGGGT GCCTAATGAG
1081 TGAGGTAACT CACATTAATT GCGTTGCGCT CACTGCCCGC TTTCCAGTCG GGAAACCTGT
1141 CGTGCCAGCT GCATTAATGA ATCGGCCAAC GCGCGGGGAG AGGCGGTTTG CGTATTGGGC
1201 GCTCTTCCGC TTCCTCGCTC ACTGACTCGC TGCGCTCGGT CGTTCGGCTG CGGCGAGCGG
1261 TATCAGCTCA CTCAAAGGCG GTAATACGGT TATCCACAGA ATCAGGGGAT AACGCAGGAA
1321 AGAACATGTG AGCAAAAGGC CAGCAAAAGG CCAGGAACCG TAAAAAGGCC GCGTTGCTGG
1381 CGTTTTTCCA TAGGCTCCGC CCCCCTGACG AGCATCACAA AAATCGACGC TCAAGTCAGA
1441 GGTGGCGAAA CCCGACAGGA CTATAAAGAT ACCAGGCGTT TCCCCCTGGA AGCTCCCTCG
1501 TGCGCTCTCC TGTTCCGACC CTGCCGCTTA CCGGATACCT GTCCGCCTTT CTCCCTTCGG
1561 GAAGCGTGGC GCTTTCTCAA TGCTCACGCT GTAGGTATCT CAGTTCGGTG TAGGTCGTTC
1621 GCTCCAAGCT GGGCTGTGTG CACGAACCCC CCGTTCAGCC CGACCGCTGC GCCTTATCCG
1681 GTAACTATCG TCTTGAGTCC AACCCGGTAA GACACGACTT ATCGCCACTG GCAGCAGCCA
1741 CTGGTAACAG GATTAGCAGA GCGAGGTATG TAGGCGGTGC TACAGAGTTC TTGAAGTGGT
1801 GGCCTAACTA CGGCTACACT AGAAGGACAG TATTTGGTAT CTGCGCTCTG CTGAAGCCAG
1861 TTACCTTCGG AAAAAGAGTT GGTAGCTCTT GATCCGGCAA ACAAACCACC GCTGGTAGCG
1921 GTGGTTTTTT TGTTTGCAAG CAGCAGATTA CGCGCAGAAA AAAAGGATCT CAAGAAGATC
1981 GTTTGATCTT TTCTACGGGG TCTGACGCTC AGTGGAACGA AAACTCACGT TAAGGGATTT
2041 TGGTCATGAG ATTATCAAAA AGGATCTTCA CCTAGATCCT TTTAAATTAA AAATGAAGTT
2101 TTAAATCAAT CTAAAGTATA TATGAGTAAA CTTGGTCTGA CAGTTACCAA TGCTTAATCA
2161 GTGAGGCACC TATCTCAGCG ATCTGTCTAT TTCGTTCATC CATAGTTGCC TGACTCCCCG
2221 TCGTGTAGAT AACTACGATA CGGGAGGGCT TACCATCTGG CCCCAGTGCT GCAATGATAC
2281 CGCGAGACCC ACGCTCACCG GCTCCAGATT TATCAGCAAT AAACCAGCCA GCCGGAAGGG
2341 CCGAGCGCAG AAGTGGTCCT GCAACTTTAT CCGCCTCCAT CCAGTCTATT AATTGTTGCC
2401 GGGAAGCTAG AGTAAGTAGT TCGCCAGTTA ATAGTTTGCG CAACGTTGTT GCCATTGCTA
2461 CAGGCATCGT GGTGTCACGC TCGTCGTTTG GTATGGCTTC ATTCAGCTCC GGTTCCCAAC
2521 GATCAAGGCG AGTTACATGA TCCCCCATGT TGTGCAAAAA AGCGGTTAGC TCCTTCGGTC
2581 CTCCGATCGT TGTCAGAAGT AAGTTGGCCG CAGTGTTATC ACTCATGGTT ATGGCAGCAC
2641 TGCATAATTC TCTTACTGTC ATGCCATCCG TAAGATGCTT TTCTGTGACT GGTGAGTACT
2701 CAACCAAGTC ATTCTGAGAA TAGTGTATGC GGCGACCGAG TTGCTCTTGC CCGGCGTCAA
2761 TACGGGATAA TACCGCGCCA CATAGCAGAA CTTTAAAAGT GCTCATCATT GGAAAACGTT
2821 CTTCGGGGCG AAAACTCTCA AGGATCTTAC CGCTGTTGAG ATCCAGTTCG ATGTAACCCA
```

```
2881 CTCGTGCACC GAACTGATCT TCAGCATCTT TTACTTTCAC CAGCGTTTCT GGGTGAGCAA
2941 AAACAGGAAG GCAAAATGCC GCAAAAAAGG GAATAAGGGC GACACGGAAA TGTTGAATAC
3001 TCATACTCTT CCTTTTTCAA TATTATTGAA GCATTTATCA GGGTTATTGT CTCATGAGCG
3061 GATACATATT TGAATGTATT TAGAAAAATA AACAAATAGG GGTTCCGCGC ACATTTCCCC
3121 GAAAAGTGCC ACCTGACGTC TAAGAAACCA TTATTATCAT GACATTAACC TATAAAAATA
3181 GGCGTATCAC GAGGCCCTTT CGTC.
```

Of particular significance are the Dra II and Nde I restriction sites. The terminator fragment was ligated with gel purified Dra II/Nde I-cut Bluescribe, thereby giving the plasmid pBST-B.

The ligation conditions generally followed were those described by Maniatis et al above, and consist of combining 100 ng of the vector pBluescribe, and 1-20 fold molar excess of the terminator fragment over vector DNA, ligation buffer [200 mM Tris-HCl, pH 7.5] and 100 mM MgCl$_2$; 20 mM dithiotheritol (DTT);
10 mM ATP, pH 7.0; and
T$_4$ DNA Ligase (1 Weiss Unit/ul) in
20.0 ul total reaction Volume pBluescribe was obtained commercially from Stratagene Cloning Systems and the procedures for growing it in bacteria, as well as isolating it using DNA by polyethylene glycol precipitation and cesium chloride centrifugation is described by Maniatis et al. above. Generally, about 10-50 ng of plasmid ligation mixture was transformed into Stratagene's JM109 competent *E. coli* cells according to the manufacturers specifications. The cells were plated onto LB ampicillin agar plates (40 ug/ml) and incubated overnight at 37° C. to select for cells harboring the plasmid.

The initiator Sau 96I/DraI fragment isolated from pEMBL8 was inserted into the plasmid, pBST-B, containing the terminator fragment. This was accomplished by treating the latter plasmid with the restriction enzyme NarI followed by Klenow filling to effect blunt ends. The conditions for this reaction are also described by Maniatis and generally consisted of;

10 ug linearized plasmid DNA;
5 ul of 10 x klenow buffer (200 mM Tris-HCl, pH 7.5, 100 mM MgCl$_2$, 20 mM DTT);
5 ul 10 mM dATP, dCTP, dGTP, and dTTP;
2 ul Klenow enzyme (1 Unit/ul); in a total Reaction Volume of 50 ul.

The reaction was conducted at room temperature for 20 min, after which it was stopped by extracting twice with distilled phenol/chloroform equilibrated with water. Next DNA was precipitated with 2.5 volumes of ethanol and ligation achieved with T$_4$ ligase as described by Maniatis et al, above. The plasmid was then reacted with calf intestinal alkaline phosphatase to dephosphorylate blunt ends and the Sau 96I/Dra I fragment ligated into the NarI site with T$_4$ ligase as described above.

The plasmid resulting from the insertion of the initiator and terminator fragments, pBSITO #12, is shown in FIG. 3 and it is apparent that these fragments are separated by the unique restriction sites, EcoRV and NdeI, as well as a 52 base pair sequence of DNA derived from the vector pBluescribe.

T$_4$ ligase was purchased from New England Biolabs. The Klenow fragment was obtained from Stratagene Cloning Systems, and calf alkaline phosphatase from Boehringer Manheim.

It will be appreciated to those skilled in the art that pBSITO #12 can be used as a source of the initiator-terminator fragment in cartridge form which is suitable for insertion into a variety of vectors, including plasmids, viruses, cosmids, etc. In the instance where it is desired that there be disposed poly-linker sites between the initiator and terminator fragments, this is readily accomplished as described below.

EXAMPLE III

Association of Poly-Linker Sites with the Terminator-Initiator Sequences

The plasmid pBSITO #12 was grown up and isolated using the procedures described in the preceding examples, and treated with the restriction enzymes NaeI and PvuI to remove the initiator and terminator fragment at the restriction sites shown in FIG. 3. The fragment was purified as described by Maniatis, et al above, and then ligated into a plasmid, pBluescript SK (M13-). The latter plasmid is useful for this procedure as it contains the intact fl origin of replication, as well as the sought after poly-linker sites. Thus by treating pBluescript SK (M13-) with NaeI and subsequent partial digestion with PvuI, it is possible to remove a segment of the origin of replication and substitute therefore the initiator-terminator fragment present in pBSITO #12 excised by similar enzymatic treatment. This yields the plasmid pPreB shown in FIG. 3. The ligation step was effected with T$_4$ ligase as described above for pBluescribe and the plasmid pBluescript SK (M13-) was obtained from Stratagene Cloning Systems. The latter company also sells pBluescript SK (fl-) as pBluescript (M13-) which is identical to pBluescript SK (fl-).

Several features of the plasmid, pPreB, are worth noting. First, it can be linearized with the enzyme EcoRV under partial digestion conditions. Second, the initiator and terminator regions enclose the viral RNA polymerase promoters, T7 and T3, and the poly-linker region associated with pBluescript SK (M13-). Also the gene encoding ampicillin resistance, and the plasmid origin of replication, ColEl, are present, as is the gene encoding beta-galactosidase.

It will be apparent to those skilled in the art that by restriction cutting pPreB, the DNA initiator-terminator cartridge shown in FIG. 3 is produced. This cartridge can be used for a variety of procedures, including cloning, subcloning, etc. after insertion into any one of a number of cloning vehicles.

EXAMPLE IV

Insertion of Initiator/Terminator DNA Cartridge into Bacteriophage Lambda-Lambda ZAP While a variety of lambda cloning vehicles can be constructed containing the initiator-terminator cartridge, we opted to construct a vector that could receive at least 10 kilobases of DNA inserted into the poly-linker region. Because lambda generally cannot exceed about 50 kilobases and still be packageable, a consideration in constructing the vector was how to reduce the size of the lambda arms to permit insertion of zero up to 10 kilobases of DNA into the poly-linker site.

FIGS. 3 and 5 show the procedures used to generate lambda arms of the desired length.

The left arm was obtained from the lambda phage, lambda L47.1, which is available from the American Type Culture Collection. A modification of Long D was used for the right arm. The left arm was generated by restriction digesting lambda L47.1 with EcoRI and Hind III, followed by SmaI treatment. This protocol is shown in FIG. 3.

FIG. 5 shows the protocol for generating lambda Long D. Wild type lambda (cI857 Sam 7) was treated with EcoRI, and the EcoRI left arm fragment was ligated to a EcORI/Hind III fragment generated by EcoRI/Hind III treatment, of the plasmid, pUC 19. Both wild type lambda and pUC 19 were obtained from Bethesda Research Labs. The wild type lambda EcoR I fragment, and the fragment containing the ECORI/Hind III sites were ligated to another lambda fragment obtained from lambda CI857 Nin4 S100 by partial digestion with Hind III followed by digestion with MluI. Ligation of these three DNA fragments results in the fragment termed lambda Long C shown in FIG. 5. Note that the Hind III junction site retains the lambda attachment site from lambda Long C. Long C contains an XhoI restriction site such that when it is treated with XhoI, followed by Klenow filling and subsequent ligation with T4 ligase, the desired lambda Long D is generated. Lambda Long C and D are available from Stratagene, San Diego.

Referring now to FIG. 3, the vector termed lambda ZAP was constructed by ligating the lambda L47.1 EcoR I/Hind III/Sma I generated left arm fragment to the initiator-terminator DNA cartridge, obtained from pPreB by linearizing the plasmid with EcoRv, and, Long D. The latter was first treated with XbaI followed by Klenow filling and MluI treatment to generate a right arm fragment that is considerably shorter in length than lambda Long D, and which can be ligated to the initiator-terminator cartridge as shown in FIG. 3 to yield lambda ZAP, The concentrations of reactants for ligating the lambda arms was generally as follows:

1.0 ug (microgram) of left lambda arm was combined with a 1 x molar concentration of right arms and at least a 1 x molar excess of cartridge DNA to vector DNA;
0.5 ul 10 x DNA ligation buffer;
0.5 ul 10 mM ATP, pH 7.0; and
1 ul T4 DNA Ligase (1 Unit/ul). The Reaction Volume was about 5.0 ul and the reaction was conducted overnight at 19° C. [Lambda ZAP is on deposit with the American Type Culture Collection and has the accession number 40298.]

EXAMPLE V

Subcloning with Lambda ZAP

FIG. 6 details the protocol wherein lambda ZAP is utilized to subclone DNA. The initial step is to construct a gene library of cDNA or genomic DNA. While a variety of procedures are available for producing either type of library, a cDNA library can be realized by isolating mRNA, particularly poly (A)+RNA by techniques well-known to those skilled in the art, for example by chromagraphy on oligo[dT]-cellulose as described by Aviv and Leder in *Proceedings of the National Academy of Sciences*, U.S.A. (1972, Vol. 69, No. 6: page 1408), and reverse transcribing the poly(A)+RNA into cDNA. The cDNA can then be introduced into a suitable site associated with the poly-linker present between the initiator and terminator regions, and lambda ZAP packaged using a suitable commercial phage packaging kit, or as described by Barbara Hohn, Methods in Enzymology, (1979, Vol. 68, p. 299) and then infected into a suitable bacterial strain, for example DP50. The latter are grown up overnight in standard growth media supplemented with 0.2% maltose and 10 millimolar magnesium sulfate, and then resuspended in 10 millimolar magnesium sulfate. The cells are incubated with lambda ZAP for approximately 15 minutes at 37 degrees Centigrade, after which three milliliters of melted top Agar (50 degrees Centigrade, 7 grams per liter agarose) was added and the mixture plated onto NZY Agar plates (NZY media with 15 grams/liter of bacto-agar).

After incubating the plates for a period of time for plaques to become apparent, 6–24 hours, they were screened to discern those harboring cDNA inserts of interest using either nucleic acid hybridization, or antibody probe techniques.

The sought-after lambda phage plaque was removed from the agar plate and resuspended in one milliliter of SM media [100 millimolar sodium chloride, 8 millimolar magnesium sulfate, 50 millimolar Tris-HCl (pH 7.5), 0.01% gelatin]. The mixture was vortexed for one minute, and contained approximately $1 \times 10^7$ phage/per milliliter. Next, approximately 200 microliters of the lambda phage stock was added to 200 microliters of host *E. coli* cells having an F1 phenotype (for example, NM522, JM109) that were grown to a density of 1 OD 600 nm in media containing 0.2% maltose, and 10 millimolar magnesium sulfate. Next, the phage were incubated with an aliquot (200 ul) of the cells for approximately 15 minutes at 32 degrees Centigrade, after which 1.6 milliliters of NZY media was added and agitated at 37 degrees Centigrade till the cells had grown up to a density of 0.3 OD 600 nm.

To the above cell suspension was added 200 microliters of a phages stock containing $1 \times 10^{11}$ M13 helper phage, and again the mixture was agitated at 37 degrees Centigrade for approximately two-six hours. The M13 helper infects bacteria and phage supplies the gene II proteins necessary for nicking, excising, and circularization of the initiator and terminator regions with intervening DNA. Because this process results in the rejoining the initiator/terminating regions it essentially produces the plasmid, pBluescript Sk (M13-), (shown in FIG. 3). The helper phage also supplies the necessary packaging functions thereby enabling the secretion of the circularized initiator-terminator plasmid. The latter is obtainable by heating the supernatant to approximately 70 degrees Centigrade for 20–30 minutes to kill the bacterial cells, and parental Lambda ZAP containing the insert DNA and then centrifuged 5 minutes at 2500 revolutions per minute. The supernatant was harvested which contains the circularized initiator-terminator molecule or pBluescript SK (M13-) in a phage coat protein.

The titer of the initiator-terminator "phage" was ascertained by adding various dilutions of the supernatant to 200 microliters of *Escherichia coli* cells grown to a density of OD 600 nm=1 containing a F' plasmid (i.e. NM522, JM109). This mixture was incubated at 37 degrees Centigrade for 10 minutes, and the cells plated on agar containing ampicillin at a concentration of 100 micrograms per milliliter. After incubation at 37 degrees Centigrade for 16 hours, colonies containing the initiator—terminator plasmid are apparent. The latter contain the gene that encodes ampicillin resistance in the intervening DNA sequence region.

EXAMPLE VI

Identification of Remote and Adjacent Chromosomal DNA Sequences Using Lambda ZAP Construction of Jumping and Junction Libraries What is described here is a method wherein a lambda ZAP-like Vector is used to determine, or map, the relative positions of DNA sequences remote from an identifiable DNA sequence. As part of this process, the location of neighboring adjacent DNA sequences is also revealed. The vector used in this process is similar to lambda ZAP less the Lac Z gene and the T3 and T7 RNA polymerase promoters.

FIGS. 7 A-E shows the general scheme whereby remote DNA sequences are identified and therefore positioned relative to a known DNA sequence. The procedure consists of cutting an organism's genome, for example the human genome, into fragments that are ligatable into circles (7B). A variety of restriction enzymes are available for this purpose. For the sake of illustration, FIG. 7A shows digestion of DNA with the enzyme, NOT I. NOT I sites are shown separating DNA sequences (probe 1,2 etc.) whose position relative to the "known gene" is to be determined. NOT I cuts DNA infrequently and generally yields fragments of a mean size of about 400-500 kilobases. The latter size range is desirable but is not a prerequisite to successfully apply the instant method.

The DNA sequences adjoining the NOT I sites are ligated to yield circular DNA wherein two sequences that were remote are now located adjacent one another (FIG. 7B). It is important that the ligation reaction be conducted at low concentrations of DNA (less than about 10 ug/ml) that favor circularization over formation of large linear DNA's resulting from the ligation of the NOT I fragments.

Figure 7C:
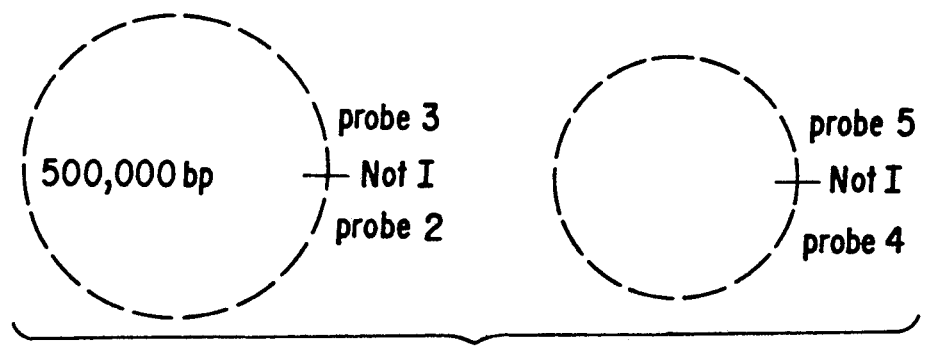
Figure 7E:
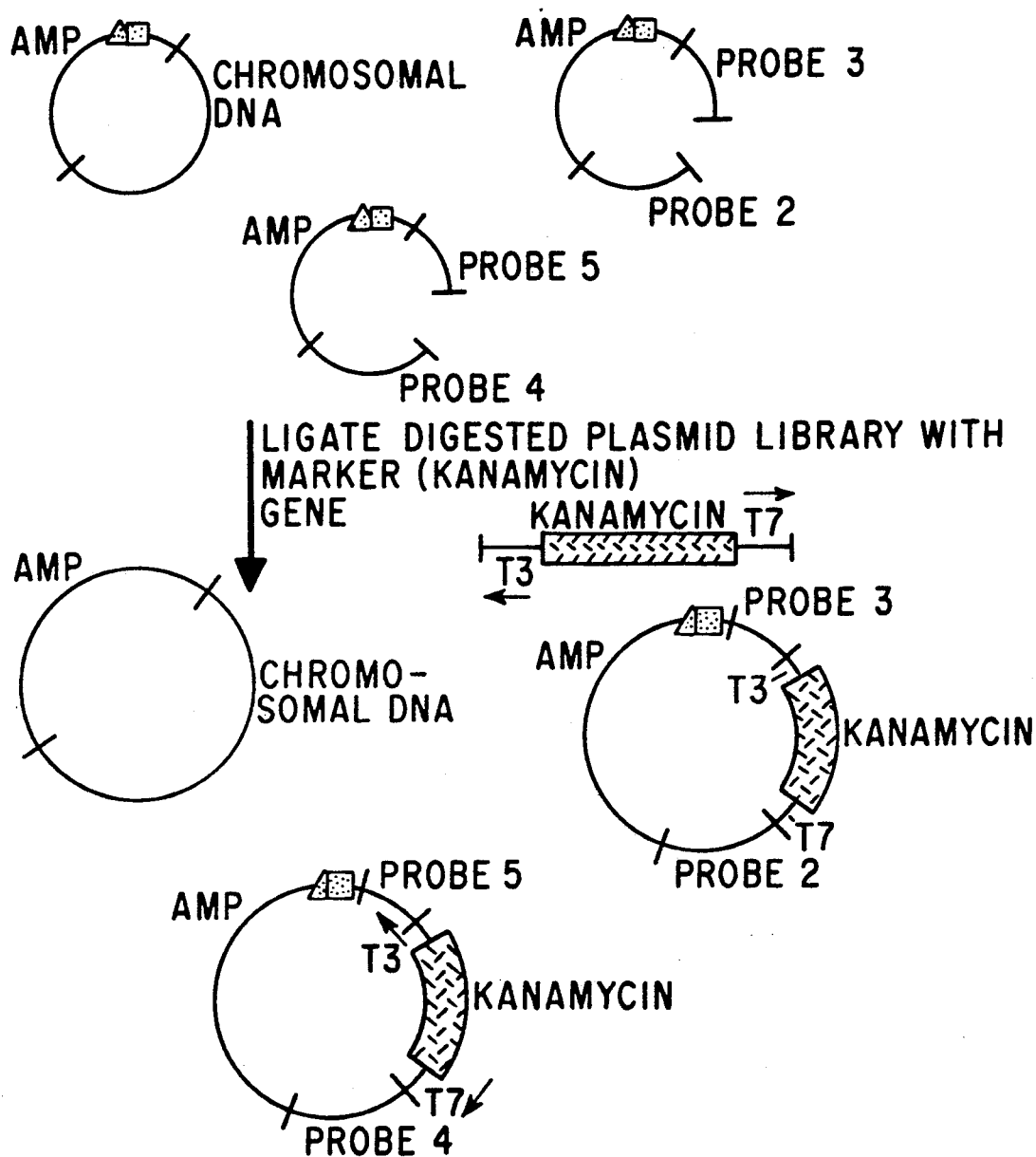

The circularized DNA is treated with a second restriction enzyme with distinct and reduced cutting specificity than the first (i.e. NOT I), to yield fragments with two remote sequences separated by NOT I sites (7C). The latter should preferably, but not necessarily, be chosen to yield DNA fragments of approximately 5 kilobases in length. A large number of enzymes are useable, and FIG. 7C diagrammatically represents this step with the enzyme MboI.

It is anticipated that fragments smaller than 5 kilobases can also be satisfactorily employed but that fragments much larger than 10 kilobases will not be because of the approximate 10 kilobase limitation on the amount of DNA that can be inserted into lambda ZAP's polylinker region (discussed above).

The lambda ZAP-like vector is subsequently treated with the enzyme BAM HI, causing a cut between the initiator and terminator fragments, (FIG. 7D) but not within the ampicillin gene region or the plasmid origin of replication. The initiator and terminator regions are depicted as a triangle and square respectively. The 5,000 base pair MboI generated fragments are ligated at the BAM HI sites following dephosphorylation with calf alkaline phosphatase, as described by Maniatis et al, above.

The ligated 5,000 base pair DNA fragments are then packaged with a suitable lambda packaging extract, and *Escherichia coli* is then infected with the resulting bacteriophage infected to amplify the gene library.

*Escherichia coli* containing the lambda ZAP-like vector and accompanying 5000 base pair fragments are co-infected with M13 helper phage. The latter produce the necessary proteins that allow for nicking, circularizing, and cleaving of the initiator and terminator regions that bracket the intervening DNA. This results in plasmids as shown in FIG. 7D wherein the DNA sequences, corresponding to probes 2, 3, 4, or 5, that were initially at opposite ends of a NOT I fragment are now adjacent one another and separated by a NOT I site. Note that there will also be present a set of plasmids that lack NOT I sites. The plasmids can be isolated (see Maniatis et al above) using standard techniques, and then subjected to NOT I treatment that cleave between the adjacent sequences, and permits the insertion of a stretch of DNA containing the T3 and T7 RNA polymerase promoters separated by a gene that codes for kanamycin resistance. This DNA construct can be generated by ligating synthetic oligonucleotides containing T3 or T7 promoter sequences to the ends of a. drug resistance gene, and then ligated to yield plasmids shown in FIG. 7E. The plasmids are then transformed into a suitable strain of Escherichia coli as described by Maniatis et al above. Cells containing plasmids with DNA sequences corresponding to those present on opposite ends of chromosomal NOT I fragments are identified by double selection in media containing ampicillin and kanamycin. It will be appreciated that the T3 and T7 RNA polymerase promoters permit the production of RNA transcripts, the latter useful as probes to detect DNA sequences that were initially at opposite ends of the large NOT I site separated DNA fragments.

Referring again to FIGS. 7A and 7E, it will be apparent that by using conventional "walking" techniques it is possible to identify sequences and to generate probes to probe 1 and probe 2 sequences. The availability of a probe to the probe 2 sequence permits plasmids to be identified from the "jumping" library (FIG. 7E, bottom) that carries the sequences corresponding to probe 3, as well as probe 2. In this manner it is possible to identify DNA sequences located at the opposite ends of large molecular weight DNA fragments. However, it is further apparent that the existence of a "jumping" library alone does not permit the continued detection of other plasmids with additional sequences located at the ends of other NOT I fragments so as to decipher their relative order. For instance, it is not possible to show that sequences corresponding to probes 4 and 5 occupy the same fragment because the position of neither probe is ascertainable relative to probe 2 or 3 sequences. This problem is obviated by creating "junction" libraries which are more efficiently constructed with the lambda ZAP technology.

The identification and generation of probes to junction sequences (i.e. probes 3 and 4 sequences) would permit the identification of plasmids in the jumping library that have at least one sequence (i.e. probe 4 and 5 sequences) in common with a junction sequence.

Figure 8A:
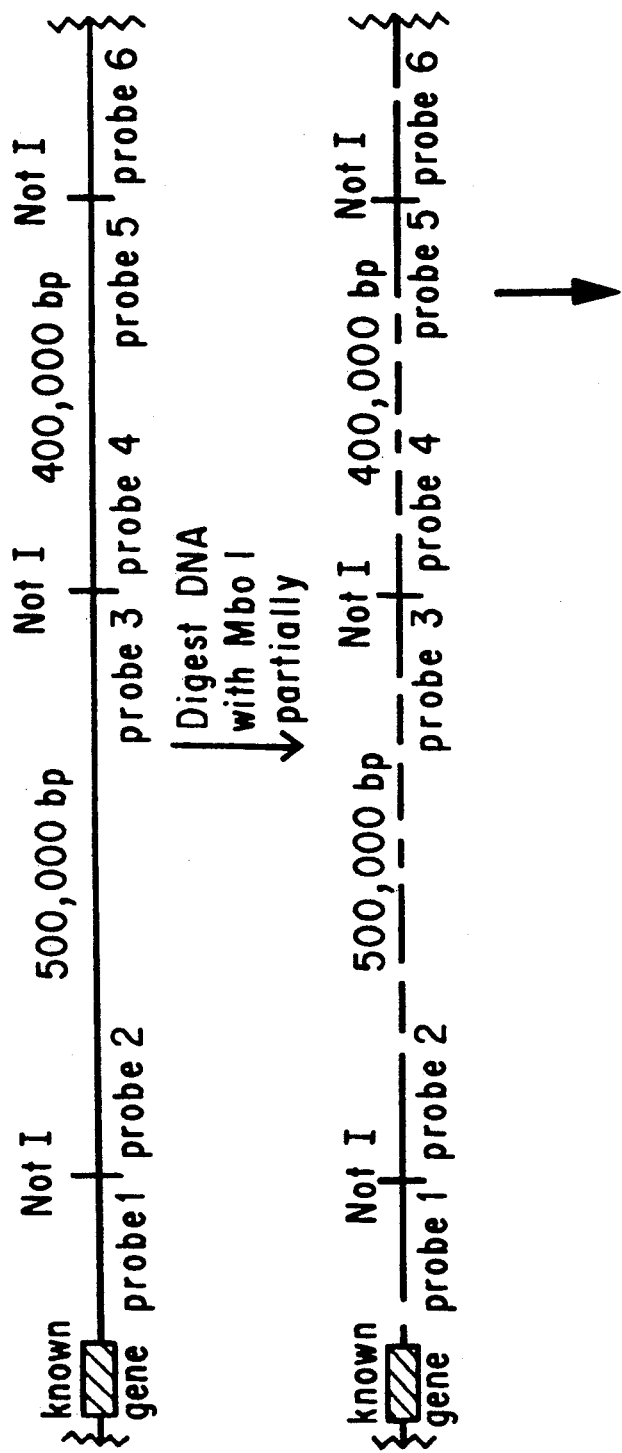
Figure 8B:
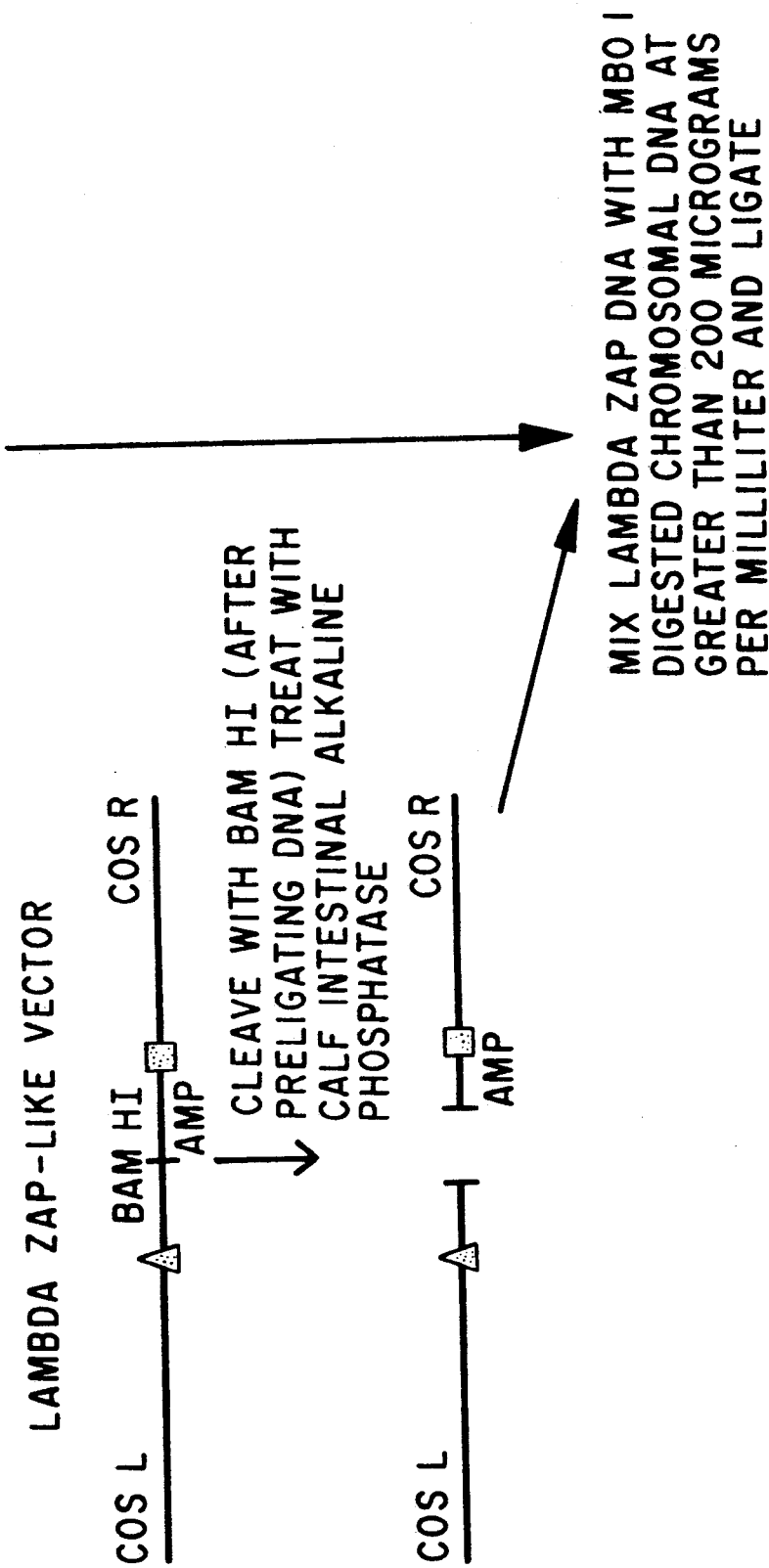
Figure 8C:
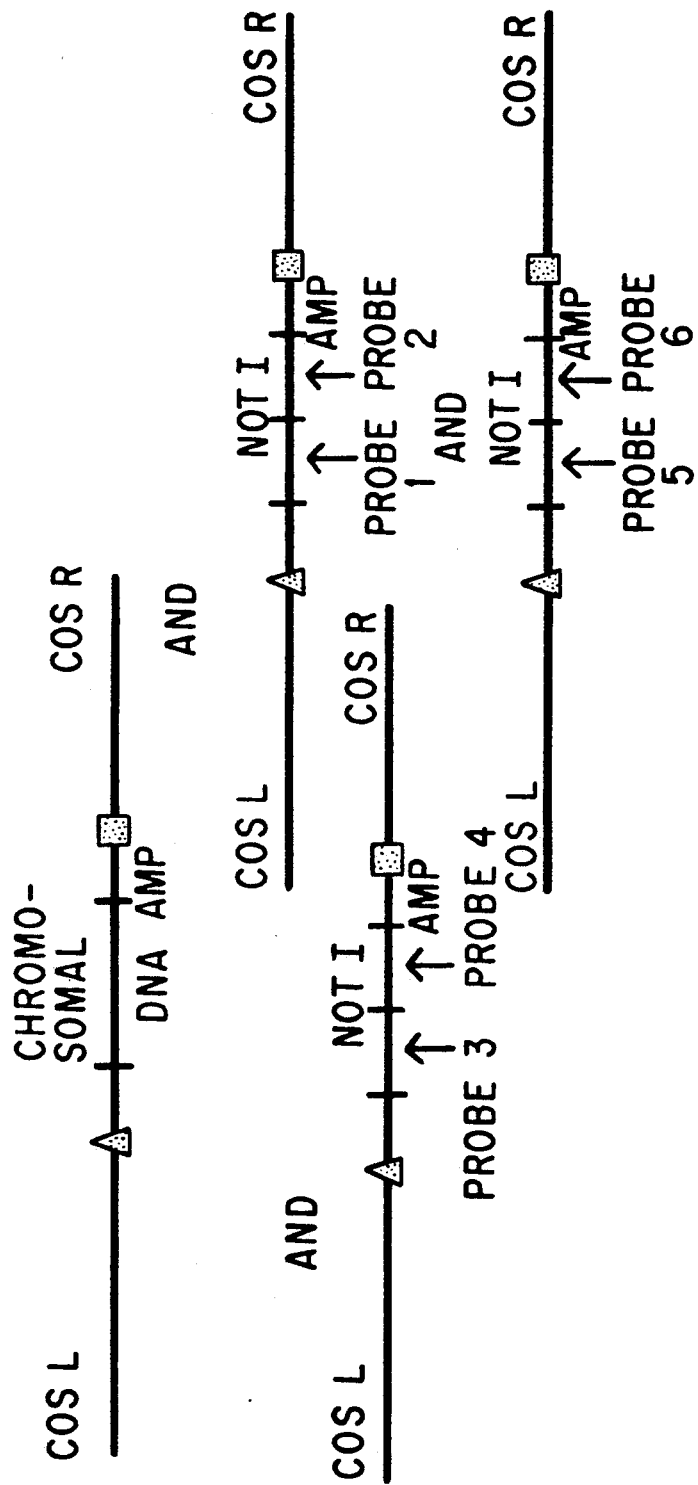
Figure 8D:
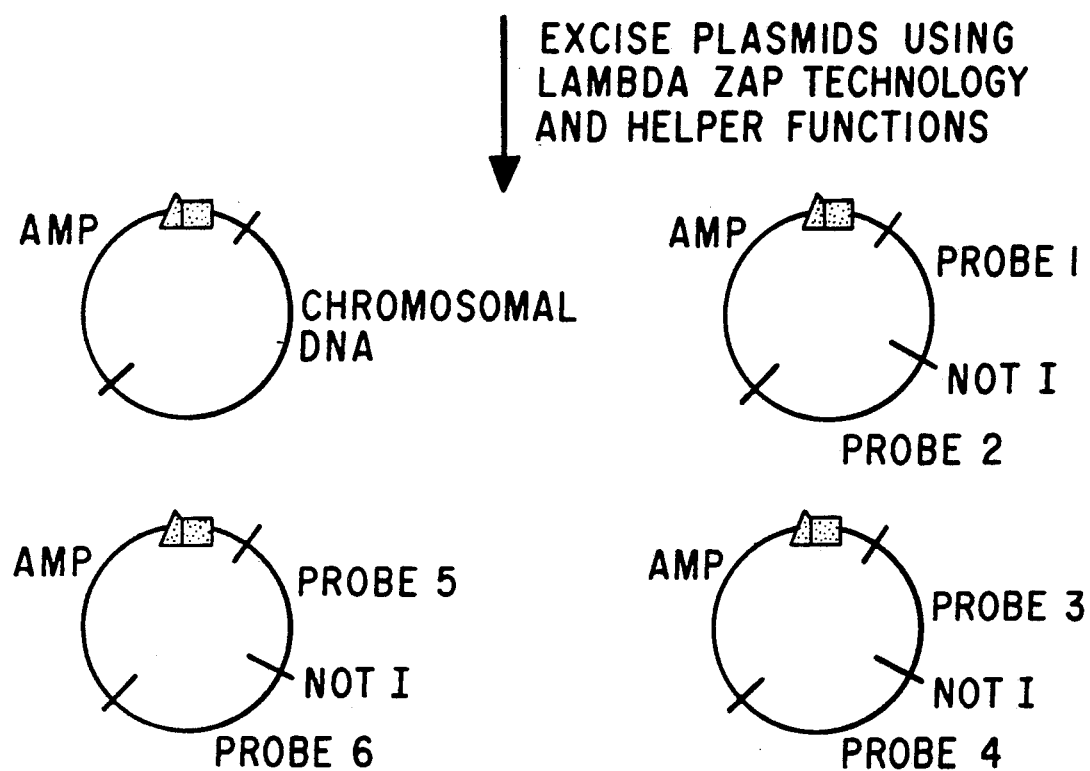
Figure 8E:
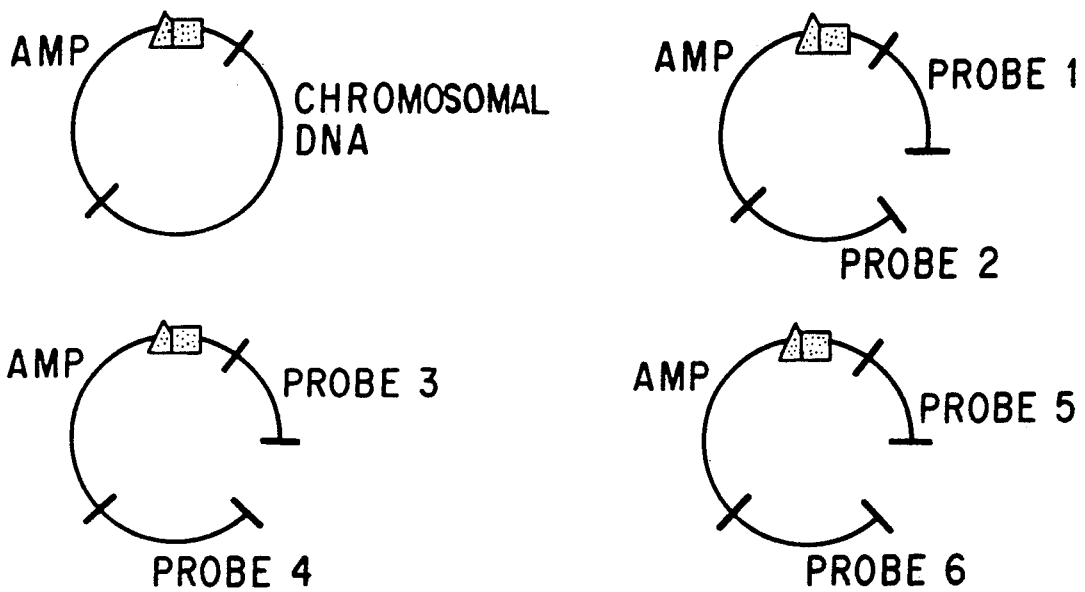
Figure 8F:
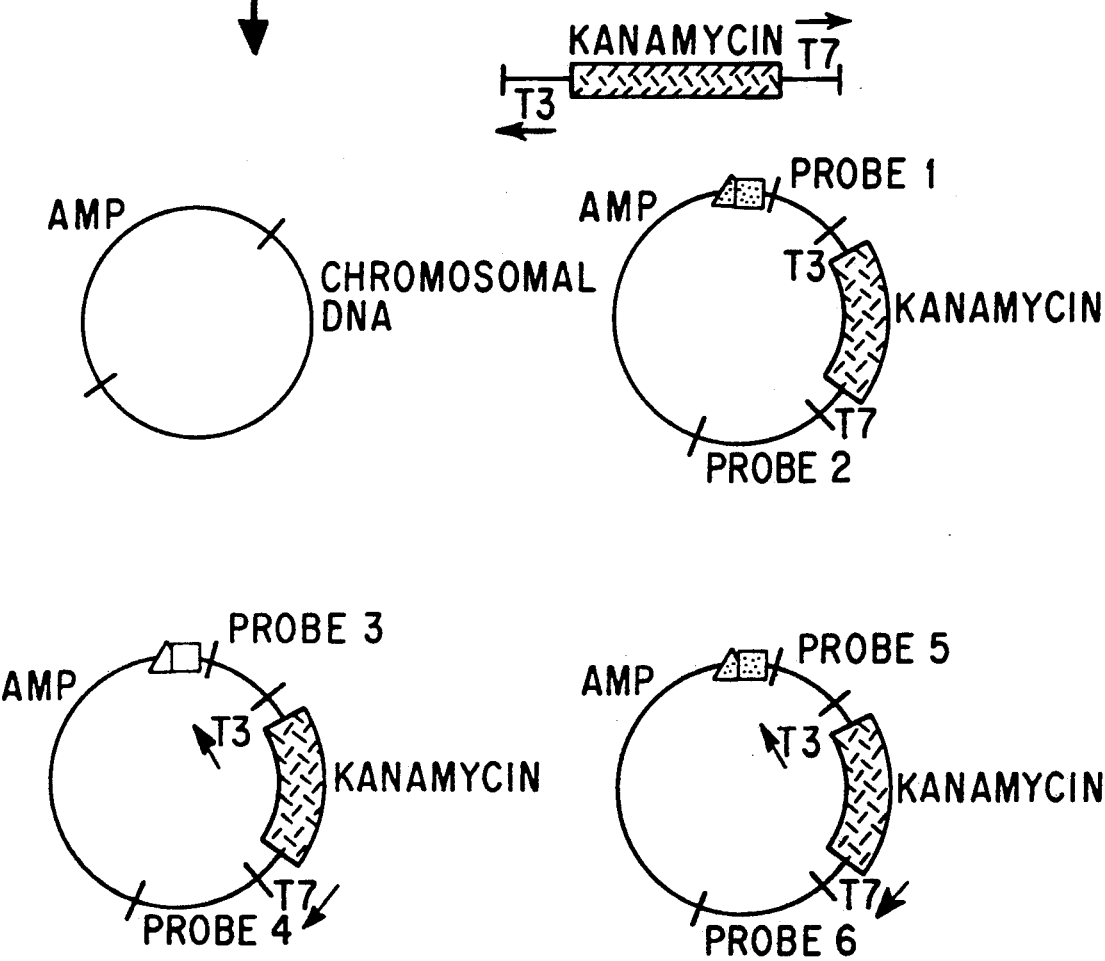

FIG. 8A shows that, to prepare a junction library, the same used for the jumping libraries digested with an enzyme that generates DNA fragments having an average length of about 5 kilobases. Mbo I can be used for this purpose. The latter are inserted into the bacteriophage lambda ZAP-like vector after the vector is cleaved at the BAM HI site situtated between the initiator and terminator regions. Before insertion of the 5 kilobase fragments, the BAM HI sites contained within the vector are dephosphorylated with calf alkaline phosphatase (FIG. 8B). Ligation is achieved by mixing the restricted lambda ZAP-like vector with Mbo I digested chromosomal DNA at a concentration of about 200 micrograms per milliliter, followed by ligation with T4 ligase. This results in lambda ZAP-like vectors as shown in FIG. 8C. It will be understood, of course, that what is shown in the figures are merely illustrative of the types of fragments that can be inserted into the vector, and by no means represents the entire spectrum of available fragments produced by enzymatic digestion.

The lambda ZAP-like vector containing the 5 kilobase fragments is packaged using a suitable commercial packaging kit, and infected into a compatible strain of Escherichia coli. The latter is used to amplify the library, which is subsequently co-infected with M13 phage that effects the nicking, circularization and cleavaging of a DNA molecule copied off of the initiator/terminator regions and intervening DNA. This results in plasmids shown in FIG. 8D. NOT I treatment of these plasmids, after isolation using standard isolation techniques, permits a stretch of DNA containing the bacteriophage RNA polymerase promoters, T3 and T7, and the gene encoding kanamycin resistance, to be inserted. Subsequent ligation yields plasmids of the type shown in FIG. 8F. These plasmids can be selected in media supplemented with both ampicillin and kanamycin. It is immediately apparent that one now has available the means, using the T3 and T7 promoters, by which to obtain RNA probes that can be used to ascertain the DNA sequences that adjoin the NOT I sites. In this way it is thus possible to "step across" naturally occurring NOT I sites (i.e. identify sequences corresponding to probes 3 and 4 etc.) thereby allowing the continued identification of plasmids having remote sequences in the jumping library.

Thus it will be appreciated that "jumping" and "junction" libraries together allow one to ascertain the presence of DNA sequences at the ends of NOT I (or other restriction enzyme fragments) and moreover, to identify DNA sequences adjacent the NOT I sites that permit one to "jump" down the chromosome.

We claim:

1. A bacteriophage lambda cloning vector that infects a host, said vector containing linear plasmid DNA flanked by filamentous phage replication initiation and termination DNA sequences oriented to permit in vivo excision and circularization of said linear plasmid DNA from said vector, said circularization producing a plasmid that replicates in said host.

2. The vector according to claim 1 wherein said replication initiation and termination DNA sequences correspond to respective replication initiation and termination sequences present in an fl origin of replication.

3. The vector according to claim 1 wherein said linear plasmid DNA contains a poly-linker.

4. The vector according to claim 1 wherein said linear plasmid DNA contains an RNA polymerase promoter.

5. The vector according to claim 1 wherein said linear plasmid DNA contains a gene coding for a selectable marker.

6. The vector according to claim 1 wherein said vector contains a DNA sequence encoding a protein that recognizes said replication initiation and termination sequences and thereby excises and circularizes said linear plasmid DNA.

7. The vector according to claim 1 wherein said vector corresponds to the vector deposit under ATCC accession number 40298.

8. A method for cloning a DNA sequence, which method comprises:
 (a) inserting said DNA sequence into the linear plasmid DNA of a vector according to claim 1,
 (b) introducing the vector of step (a) containing said inserted DNA sequence into a host bacterial cell, and
 (c) introducing into said host cell a bacteriophage capable of expressing a protein which recognizes said replication initiation and termination sequences of said vector and effects the in vivo excision and circularization of said linear plasmid DNA from said vector.

* * * * *